US011419914B2

(12) United States Patent
Fein

(10) Patent No.: US 11,419,914 B2
(45) Date of Patent: Aug. 23, 2022

(54) SAFE DESMOPRESSIN ADMINISTRATION

(71) Applicant: Serenity Pharmaceuticals LLC, Milford, PA (US)

(72) Inventor: Seymour Fein, New Canaan, CT (US)

(73) Assignee: Serenity Pharmaceuticals LLC, Mississauga (CA)

(*) Notice: Subject to any disclaimer, the term of this patent is extended or adjusted under 35 U.S.C. 154(b) by 0 days.

(21) Appl. No.: 15/400,535

(22) Filed: Jan. 6, 2017

(65) Prior Publication Data

US 2018/0369320 A1    Dec. 27, 2018

Related U.S. Application Data

(62) Division of application No. 13/378,778, filed as application No. PCT/US2010/038663 on Jun. 15, 2010, now Pat. No. 9,539,302.

(60) Provisional application No. 61/268,954, filed on Jun. 18, 2009.

(51) Int. Cl.
| *A61K 38/11* | (2006.01) |
| *A61K 38/095* | (2019.01) |
| *A61K 9/00* | (2006.01) |
| *A61M 15/08* | (2006.01) |
| *A61M 11/06* | (2006.01) |
| *A61M 11/00* | (2006.01) |

(52) U.S. Cl.
CPC .......... *A61K 38/095* (2019.01); *A61K 9/0043* (2013.01); *A61M 15/08* (2013.01); *A61M 11/008* (2014.02); *A61M 11/06* (2013.01)

(58) Field of Classification Search
None
See application file for complete search history.

(56) References Cited

U.S. PATENT DOCUMENTS

| 3,980,631 A | 9/1976 | Prochazka et al. |
| 4,148,787 A | 4/1979 | Mulder et al. |
| 4,263,283 A | 4/1981 | Cort |
| 4,285,858 A | 8/1981 | Cort et al. |
| 4,548,922 A | 10/1985 | Carey et al. |
| 4,572,832 A | 2/1986 | Kigasawa et al. |
| 4,746,508 A | 5/1988 | Carey et al. |
| 4,764,378 A | 8/1988 | Keith et al. |
| 4,860,738 A | 8/1989 | Hegemann et al. |
| 4,863,737 A | 9/1989 | Stanley et al. |
| 4,878,892 A | 11/1989 | Sibalis et al. |
| 4,944,429 A | 7/1990 | Bishop et al. |
| 5,023,252 A | 6/1991 | Hseih |
| 5,047,398 A | 9/1991 | Hagstam et al. |
| 5,112,804 A | 5/1992 | Kowarski |
| 5,122,383 A | 6/1992 | Heiber et al. |
| 5,135,480 A | 8/1992 | Bannon et al. |
| 5,154,122 A | 10/1992 | Goldschmidt |
| 5,212,199 A | 5/1993 | Heiber et al. |
| 5,227,169 A | 7/1993 | Heiber et al. |
| 5,288,497 A | 2/1994 | Stanley et al. |
| 5,298,256 A | 3/1994 | Flockhart et al. |
| 5,314,694 A | 5/1994 | Gale et al. |
| 5,350,741 A | 9/1994 | Takada |
| 5,388,766 A | 2/1995 | Buisson |
| 5,464,387 A | 11/1995 | Haak et al. |
| 5,482,931 A | 1/1996 | Harris et al. |
| 5,498,598 A | 3/1996 | Harris |
| 5,500,413 A | 3/1996 | Larsson et al. |
| 5,576,014 A | 11/1996 | Mizumoto et al. |
| 5,631,246 A | 5/1997 | Hashemi et al. |
| 5,707,648 A | 1/1998 | Yiv |
| 5,719,122 A | 2/1998 | Chiodini et al. |
| 5,731,303 A | 3/1998 | Hsieh |
| 5,746,508 A | 5/1998 | Chin, Jr. |
| 5,763,405 A | 6/1998 | Fjellestad-Paulsen et al. |
| 5,780,434 A | 7/1998 | Fjellestad-Paulsen |
| 5,848,991 A | 12/1998 | Gross et al. |
| 5,849,322 A | 12/1998 | Ebert et al. |
| 5,860,567 A | 1/1999 | Fuchs et al. |
| 5,927,559 A | 7/1999 | Bommer et al. |
| 5,929,027 A | 7/1999 | Takama et al. |
| 5,985,835 A | 11/1999 | Larsson et al. |
| 5,988,449 A | 11/1999 | Fuchs et al. |
| 5,990,273 A | 11/1999 | Andersson et al. |

(Continued)

FOREIGN PATENT DOCUMENTS

| CN | 1233952 | 11/1999 |
| CN | 1060980 | 1/2001 |

(Continued)

OTHER PUBLICATIONS

Agnoli G.C. et al., (2002) "Low-dose desmopressin infusion: renal action in healthy women in moderate salt retention and depletion, and interactions with prostanoids," Prostaglandins Leukotrienes and Essential Fatty Acids, 67(4):263-273.

Ault, Alicia, "FDA advisers reject desmopressin for nocturia." American Pharmacist Association, press release of Jan. 14, 2015, available online at https://www.pharmacist.com/fda-advisers-reject-desmopressin-nocturi.

Bommer, Rene et al., "Preservative-Free Nasal Drug-Delivery Systems," Medical Device Technology, Oct. 2004, 2-5.

Desmopressin Acetate for Desmopressin Injection: revised in Aug. 1998, intranasal: revised in Jul. 1999, Spray: created in Oct. 1999; Drugs in Japan Ethical Drugs, Japan, Yakuii -Jihosha, Inc., (in Japanese; with English translation attached) 13 pages.

(Continued)

*Primary Examiner* — Fred H Reynolds
(74) *Attorney, Agent, or Firm* — Goodwin Procter LLP

(57) ABSTRACT

Disclosed is a family of intranasal spray dispensers for administering uniform low doses of desmopressin so as to achieve safe antidiuresis in human patients. The dispensers of the invention may be used in the treatment of nocturia, primary nocturnal enuresis, incontinence, urinary frequency, diabetes insipidus, or any disease or syndrome where desmopressin therapy is useful or where safe temporary suppression of urine production may lead to beneficial health effects or increased convenience in voiding control.

19 Claims, 10 Drawing Sheets
(2 of 10 Drawing Sheet(s) Filed in Color)

(56) References Cited

U.S. PATENT DOCUMENTS

| | | |
|---|---|---|
| 6,180,608 B1 | 1/2001 | Gefter et al. |
| 6,200,602 B1 | 3/2001 | Watts et al. |
| 6,227,413 B1 | 5/2001 | Bommer |
| 6,248,358 B1 | 6/2001 | Bologna et al. |
| 6,264,981 B1 | 7/2001 | Zhang et al. |
| 6,321,942 B1 | 11/2001 | Krampen et al. |
| 6,352,181 B1 | 3/2002 | Eberhard et al. |
| 6,355,270 B1 | 3/2002 | Ferrari et al. |
| 6,418,925 B1 | 7/2002 | Genova et al. .......... 128/200.14 |
| 6,446,839 B1 | 9/2002 | Ritsche |
| 6,605,060 B1 | 8/2003 | O'Neil .......................... 604/152 |
| 6,693,082 B2 | 2/2004 | Alonso et al. |
| 6,705,493 B2 | 3/2004 | Mijers |
| 6,708,846 B1 | 3/2004 | Fuchs et al. |
| 6,746,678 B1 | 6/2004 | Shapiro |
| 6,772,915 B2 | 8/2004 | Helmlinger |
| 6,872,405 B2 | 3/2005 | Takaishi et al. |
| 7,112,561 B2 | 9/2006 | Gyurik et al. |
| 7,182,226 B2 | 2/2007 | Mbonyumuhire |
| 7,201,296 B2 | 4/2007 | Graf |
| 7,244,703 B2 | 7/2007 | Gyurik ................. A61K 9/0043 514/1.1 |
| 7,335,186 B2 | 2/2008 | O'Neil |
| 7,405,203 B2 | 7/2008 | Fein |
| 7,579,321 B2 | 8/2009 | Fein ..................... A61K 9/0056 514/1.1 |
| 7,799,761 B2 | 9/2010 | Fein ..................... A61K 9/0056 514/10.9 |
| 8,143,225 B2 | 3/2012 | Fein |
| 8,399,410 B2 | 3/2013 | Herschkowitz et al. |
| 9,375,530 B2 | 6/2016 | Herschkowitz et al. |
| 9,539,302 B2 | 1/2017 | Fein |
| 2002/0013262 A1 | 1/2002 | Alonso et al. |
| 2003/0232078 A1 | 12/2003 | Dong et al. |
| 2004/0138098 A1 | 7/2004 | Fein |
| 2005/0002927 A1 | 1/2005 | Quay et al. |
| 2005/0025824 A1 | 2/2005 | Percel et al. |
| 2005/0127107 A1 | 6/2005 | Mbonyumuhire et al. |
| 2005/0158247 A1 | 7/2005 | Veronesi et al. |
| 2005/0232867 A1 | 10/2005 | Gyurik et al. |
| 2007/0111964 A1 | 5/2007 | Feller et al. |
| 2007/0262090 A1 | 11/2007 | Ritsche |
| 2007/0265207 A1 | 11/2007 | Fein |
| 2007/0284393 A1 | 12/2007 | Ritsche et al. |
| 2008/0035223 A1 | 2/2008 | Ritsche et al. |
| 2008/0119408 A1 | 5/2008 | Costantino et al. |
| 2008/0274951 A1 | 11/2008 | Fein |
| 2008/0299079 A1 | 12/2008 | Meezan et al. |
| 2009/0005432 A1 | 1/2009 | Fein |
| 2009/0026289 A1 | 1/2009 | Nadler et al. |
| 2009/0035260 A1 | 2/2009 | Veronesi et al. |
| 2009/0042970 A1 | 2/2009 | Herschkowitz et al. |
| 2009/0119408 A1 | 5/2009 | Teze et al. |
| 2010/0056436 A1 | 3/2010 | Fein |
| 2010/0160214 A1 | 6/2010 | Fein et al. |
| 2012/0015880 A1 | 1/2012 | Fein ..................... A61K 9/0043 514/10.9 |
| 2012/0149643 A1 | 6/2012 | Fein |
| 2012/0322734 A1 | 12/2012 | Fein ..................... A61K 9/0056 514/10.9 |
| 2015/0031613 A1 | 1/2015 | Fein ..................... A61K 9/0043 514/10.9 |
| 2018/0369320 A1 | 12/2018 | Fein |

FOREIGN PATENT DOCUMENTS

| | | |
|---|---|---|
| CN | 1060980 C | 1/2001 |
| CN | 1233952 C | 12/2005 |
| CN | 1785448 | 6/2006 |
| CN | 1785448 A | 6/2006 |
| EP | 0517211 A1 | 12/1992 |
| EP | 943336 A1 | 9/1999 |
| EP | 0943336 A1 | 9/1999 |
| EP | 1093818 A1 | 4/2001 |
| EP | 1347781 A1 | 10/2003 |
| EP | 1466626 A1 | 10/2004 |
| EP | 1501534 A2 | 2/2005 |
| JP | S63-501954 | 8/1988 |
| JP | S63501954 A | 8/1988 |
| JP | 3246233 A | 11/1991 |
| JP | H03246233 A | 11/1991 |
| JP | H5-509241 | 12/1993 |
| JP | H05509241 A | 12/1993 |
| JP | H11-500646 | 1/1999 |
| JP | H11500646 A | 1/1999 |
| JP | 2007-517067 | 6/2007 |
| JP | 2007-517067 A | 6/2007 |
| WO | WO-1987/003473 A1 | 6/1987 |
| WO | WO-1991/014468 A1 | 10/1991 |
| WO | WO-1995/001183 A1 | 1/1995 |
| WO | WO-1995/001373 A1 | 1/1995 |
| WO | WO-199501183 A1 | 1/1995 |
| WO | WO-1995/018602 A1 | 7/1995 |
| WO | WO-1995018602 A1 | 7/1995 |
| WO | WO-1996/040332 A1 | 12/1996 |
| WO | WO-97/48379 | 12/1997 |
| WO | WO-1997/048379 A1 | 12/1997 |
| WO | WO-1998/001159 A2 | 1/1998 |
| WO | WO-1998001159 A2 | 1/1998 |
| WO | WO-1999/013864 A2 | 3/1999 |
| WO | WO-1999013664 A2 | 3/1999 |
| WO | WO-2000/0044351 A1 | 8/2000 |
| WO | WO-200044351 A1 | 8/2000 |
| WO | WO-2000/059423 A1 | 10/2000 |
| WO | WO-2000/061117 A1 | 10/2000 |
| WO | WO-200059423 A1 | 10/2000 |
| WO | WO-200061117 A1 | 10/2000 |
| WO | WO-2001/037808 A1 | 5/2001 |
| WO | WO-2001037808 A1 | 5/2001 |
| WO | WO-2001/039749 A2 | 6/2001 |
| WO | WO-2001039749 A2 | 6/2001 |
| WO | WO-2002/013782 A1 | 2/2002 |
| WO | WO-2002013782 A1 | 2/2002 |
| WO | WO-2003/094886 A2 | 11/2003 |
| WO | WO-2003094886 A2 | 11/2003 |
| WO | 2004-014411 | 2/2004 |
| WO | WO-2004/014411 A1 | 2/2004 |
| WO | WO-2004/041153 A2 | 5/2004 |
| WO | WO-2004041153 A2 | 5/2004 |
| WO | 1466626 A1 | 10/2004 |
| WO | WO-2005/046707 A1 | 5/2005 |
| WO | WO-2005046707 A1 | 5/2005 |
| WO | WO-2005/065435 A2 | 7/2005 |
| WO | WO-2007/146126 A2 | 12/2007 |
| WO | 2009-003199 | 12/2008 |
| WO | WO-2009/003199 A1 | 12/2008 |
| WO | WO-2009/021007 A1 | 2/2009 |
| WO | 2010-075327 | 7/2010 |
| WO | WO-2010/075266 A2 | 7/2010 |
| WO | WO-2010/075327 A1 | 7/2010 |
| WO | WO-2010075266 A2 | 7/2010 |
| WO | WO-2010/147981 A1 | 12/2010 |
| WO | WO-2010147981 A1 | 12/2010 |

OTHER PUBLICATIONS

Desmopressin Spray 2.5 Kyowa Package Insert, DDAVP Spray, (in Japanese; with English translation attached) 12 pages, 2012.

Dixon et al. (1981) "The Effect of DDAVP on Intravenous Urography," British Journal of Radiology, 54:484-487.

Fabrizio B. et al., (2009) "In vitro permeation of desmopressin across rabbit nasal mucosa from liquid nasal sprays: The enhancing effect of potassium sorbate," European Journal of Pharmaceutical Sciences, 37(1):36-42.

Fejellestad-Paulsen (1996) "Absorption and Metabolism of Neurohypophyseal Hormones, with C6 special reference to Desmopressin (dDAVP), in Human Tissue and after various Routes of Administration" (Doctoral Dissertation).

Fjellestad-Paulsen (1993 "Pharmacokinetics of 1-desamino-8-d-arginine vasopressin after various routes of administration in healthy volunteers," Clinical Endocrinology, 38 p. 177-182.

(56) References Cited

OTHER PUBLICATIONS

Grossman A. et al., "Two New Modes of Desmopressin (DDAVP) Administration," *British Medical Journal*, vol. 280, No. 6225, 1980, p. 1215.

Guo et al., (2006), "The Influence of Actuation Parameters on In Vitro Testing of Nasal Spray Products" J. Pharm. Sci., 95:2029-2040, abstract only.

Guo et al., (2008), "Assessment of the Influence Factors on In Vitro Testing of Nasal Sprays Using Box-Behnken Experimental Design" Eur. J. Pharm. Sci., 35:417-426.

Hammer and Vilhardt. (1985) "Peroral Treatment of Diabetes Insipidus with a Polypeptide Hormone Analog, Desmopressin," *The Journal of Pharmacology and Experimental Therapeutics*. 234:754-760.

Ilan et al. (1996) "Improved Oral Delivery of Desmopressin via a Novel Vehicle: Mucoadhesive Submicron Emulsion," *Pharmaceutical Research* 13(7):1083-1087.

Jahr et al., (1992) "Effect of Desmopressin Acetate on Hindlimb Perfusion Pressure in Rats: What is the Mechanism?" Anesth. Analg., 75:411-415.

Janknegt et al., (1997) "Oral Desmopressin as a New Treatment Modality for Primary Nocturnal Enuresis in Adolescents and Adults: A Double-Blind, Randomized, Multicenter Study" Journal of Urology, 157(2):513-517.

Kinter and Beeuwkes (1982) "Oral antidiuretic therapy: studies in the diabetes insipidus rat," *American Physiological Society* 12(3):R491-R499.

Klocker et al, "Antimicrobial Safety of a Preservative-Free Nasal Multiple-Dose Drug Administration System," European Journal of Pharmaceutics and Biopharmaceutics, 2004, 489-493, 57.

Kohler et al. (1988) "Pharmacokinetics and haematological effects of desmopressin" Eur.J.Clin. Pharmacol. 35: 281-285.

Laczi et al. (1980) "Effects of vasopressin analogues (DDAVP, DVDAVP) in the form of sublingual tablets in central diabetes insipidus" International Journal of Clinical Pharmacology, Therapy and Toxicology. 12:63-68.

Law et al. ,(2001) "Preparation of desmopressin-containing liposomes for intranasal delivery," *Journal of Controlled Release* 70:375-382.

Le Tourneau, Christophe et al. "Dose escalation methods in phase 1 clinical cancer trials," J. Natl. Cancer Inst. (2009) 101 p. 708-720.

Lefebvre, Arthur H., Atomization and Sprays (1989) ISBN 0-89116-603-3, pp. 112-113.

Malan et al. (1994) "Subcutaneous Administration of Desmopressin as a Test of Maximal Urinary Concentrating Ability in the Fischer 344 Rat," Toxicology Methods, 4( 3):188-192.

Minirin Nasal Spray, Ferring Pharmaceuticals. Internet document http://www.medsafe.gov.nz/Consumers/CMI/m/MinirinNSpray.htm May 3, 2001; accessed Oct. 4, 2007; 3 pages.

Olanoff L.S. et al., "Effect of Intranasal Histamine on Nasal Mucosal Blood Flow and the Antidiuretic Activity of Desmopressin," *J. Clin. Invest.*, 1987, vol. 80, pp. 890-895.

Patent Cooperation Treaty (PCT) International Preliminary Report on Patentability; International Application No. PCT/US2009/068962, dated Jun. 29, 2011, 10 pages.

Patent Cooperation Treaty (PCT) International Search Report; International Application No. PCT/US2003/014463, dated May 27, 2004, 2 pages.

Patent Cooperation Treaty (PCT) International Search Report; International Application No. PCT/US2003/035662, dated Sep. 30, 2004, 1 page.

Patent Cooperation Treaty (PCT) International Search Report; International Application No. PCT/US2009/068962, dated Nov. 19, 2010, 4 pages.

Patent Cooperation Treaty (PCT) International Search Report and Written Opinion for International Application No. PCT/US2010/038663, dated Aug. 10, 2010, 9 pages.

Penington et al., (2008), Abstract of "Spray Pattern and Droplet Size Analyses for High Shear Viscosity Determination of Aqueous Suspension Corticosteroid Nasal Sprays," Drug. Dev. Ind. Pharm., 24:923-929.

Request for Ex Parte Re-Examination of U.S. Pat. No. 7,405,203 filed Oct. 12, 2011, 42 pages.

Shi, Huawei, PhD thesis (2006) North Carolina State University "Numerical simulation of airflow, particle deposition and drug delivery in a representative human nasal airway model."

Supplementary European Search Report ands Search Opinion for European Patent Application No. 10790053.2 dated Jul. 3, 2013 (6 pages).

Supplementary European Search Report and Search Opinion for European Patent Application No. 17168865.8 dated Nov. 9, 2017 (6 pages).

Svedman et al., (1991) "Administration of antidiuretic peptide (DDAVP) by way of suction deepithelialised skin" The Lancet, 337:1506-1509.

Swain (1999) "Blister Packaging Leads the Way: Despite continuous pressure to contain costs, the demand for pharmaceutical packages keeps growing" Pharma and Medical Packaging News Magazine (4 pages).

Tormey & O'Laoire (1992) "Severe Prolonged Antidiuresis Following Desmopressin and Carbamazepine Interaction in Postoperative Diabetes Insipidus," *European Journal of Internal Medicine*, vol. 3, pp. 341-343.

Trinh-Trang-Tan et al., (2000) "Regulation of UT-A2 Protein in vivo and in vitro," Journal of the American Society of Nephrologv, vol. 11, No. Program and Abstract Issue, DD. 23A.

Weiss et al. (2012) "Desmopressin Orally Disintegrating Tablet EffectivelyReduces Nocturia: Results of a Randomized, Double-Blind, Placebo-Controlled Trial" Neurourology and Urodvnamics 31:441-447.

Williams et al. (1986) "Antidiuretic Effect and Pharmacokinetics of Oral 1-Desamino-8-D-Arginine Vasopressin. 1. Studies in Adults and Children," *Journal of Clinical Endocrinology and Metabolism* 63:129-132.

Wolfson et al. ,(1979) "Mechanism of Vasopressin Inhibition of Pancreatic Secretion," *American Journal of Gastroenterology*, vol. 71, No. 5, pp. 490-495.

Written Opinion for Singapore Patent Application No. 201104611.7, dated Jun. 12, 2012, 7 pages.

Agnoli G.C. et al., (2002) "Low-dose desmopressin infusion: renal action in healthy women in moderate salt retention and depletion, and interactions with prostanoids," *Prostaglandins Leukotrienes and Essential Fatty Acids*, 67(4):263-273.

Desmopressin Acetate for Desmopressin Injection: revised in Aug. 1998, Intranasal: revised in Jul. 1999, Spray: created in Oct. 1999; *Drugs in Japan Ethical Drugs*. Japan, Yakuji—Jihosha, Inc., (in Japanese; with English translation attached) 13 pages.

Desmopressin Spray 2.5 Kyowa Package Insert, DDAVP Spray, (in Japanese; with English translation attached) 12 pages.

Fjellestad-Paulsen (1996) "Absorption and Metabolism of Neurohypophyseal Hormones, with special reference to Desmopressin (dDAVP), in Human Tissue and after various Routes of Administration," (Doctoral Dissertation).

Fjellestad-Paulsen et al., (1993) "Pharmacokinetics of 1-deamino-8-D-arginine vasopressin after various routes of administration in healthy volunteers," *Clinical Endocrinology* 38:177-182.

Grossman A. et al., (1980) "Two New Modes of Desmopressin (DDAVP) Administration," *British Medical Journal*, 280(6225):1215.

Jahr et al., (1992) "Effect of Desmopressin Acetate on Hindlimb Prefusion Pressure in Rats: What is the Mechanism?" *Anaesth. Analg.*, 75: 411-415.

Kohler et al. (1988) "Pharmacokinetics and haemotological effects of desmopressin," *Eur .J .Clin. Pharmacol.*, 35:261-265.

Laczi et al. (1980) "Effects of vasopressin analogues (DDVAP, DVDAVP) in the form of sublingual tablets in central diabetes insipidus," *International Journal of Clinical Pharmacology, Therapy and Toxicology*. 12:63-68.

"Minirin Nasal Spray," Ferring Pharmaceuticals, Internet document <<http://www.medsafe.gov.nz/Consumers/CMI/m/MiniriNSpray.htm>&g-t, May 3, 2001; accessed Oct. 4, 2007; 3 pages.

Olanoff L.S. et al., (1987) "Effect of Intranasal Histamine on Nasal Mucosal Blood Flow and the Antidiuretic Activity of Desmopressin," *J. Clin. Invest.*, 80:890-895.

(56) References Cited

OTHER PUBLICATIONS

Tormey & O'Laoire (1992) "Severe Prolonged Antidiuresis Following Desmopressin and Carbamazepine Interaction in Postoperative Diabetes Insipidus," *European Journal of Internal Medicine*, 3: 341-343.
Trinh-Trang-Tan et al., (2000) "Regulation of UT-A2 Protein In vivo and In vitro," *Journal of the American Society of Nephrology*, vol. 11, No. Program and Abstract Issue, pp. 23A.
Weiss et al. (2012) "Desmopressin Orally Disintegrating Tablet Effectively Reduces Nocturia: Results of a Randomized, Double-Blind, Placebo-Controlled Trial," *Neurology and Urodynamics* 31:441-447.
Wolfson et al., (1979) "Mechanism of Vasopressin Inhibition of Pancreatic Secretion," *American Journal of Gastroenterology*, 71(5):490-495.
Klocker, Norbert et al, Antimicrobial Safety of a Preservative-Free Nasal Mltiple-Dose Drug Administration System, European Journal of Pharmaceutics and Biopharmaceutics, 2004, 489-493, 57.
Search Report for Chinese Patent Application No. 200980156096.8, dated Dec. 21, 2009, 2 pages.
Ault, Alicia, "FDA advisers reject desmopressin for nocturia." American Pharmacist Association, press release of Jan. 14, 2015, available online at https://www.pharmacist.com/fda-advisers-reject-desmopressin-nocturia.
Lefebvre, Arthur H., Atomization and Sprays (1989) ISBN 0-89116-603-3.
Law, S. L. et al; "Preparation of desmopressin-containing liposomes for intranasal delivery." J. Control. Rel. (2001) 70 p. 375-382.
Fjellestad-Paulsen, A. et al; "Pharmacokinetids of 1-desamino-8-d-arginine vasopressin after various routes of administration in healthy volunteers," Clinical Endocrinology (1993) 38 p. 177-182.
"Bentley Pharm Receives Broad U.S. Patent Protection for Its Intranasal Drug Delivery Technology," *Reuters*, Jul. 19, 2007 (D6 from EP 2442821 Opposition).
Charnow, (2018), "Desmopressin Nasal Spray Improves Nocturia in the Elderly" *Renal and Urology News*. (D29 in EP244821 Opposition).
Communication of Notices of Opposition filed in European Patent No. EP 2442821 on Mar. 3, 2018, by Ferring B.V. (1 page).
"CPEX Pharmaceuticals and Serenity Pharmaceuticals Announce Collaboration on Drug Candidate for Urology Indication," Aug. 4, 2008 (D6 from EP 2442821 Opposition).
CPEX Pharmaceuticals, Inc. Form 10-K for the Fiscal Year Ending 2008 filed with the U.S. Securities and Exchange Commission (D6 from EP 2442821 Opposition).
Day, N., (2009), "Chapter 13: Aqueous Nasal Dosage Forms," in *Pharmaceutical Preformulation and Formulation*, Ed: M. Gibson, CRC Press, pp. 456-474 (D22 in EP2442821 Opposition).
Declaration of Wendy Murray under 37 C.F.R. § 132 submitted in U.S. Appl. No. 13/378,778, filed Jul. 5, 2016 (5 pages; D31 in EP 2442821 Opposition).
Desmopressin Spray 2.5 Kyowa, pp. 1-4, revised Oct. 2008 (D12 from EP 2442821 Opposition), including English translation submitted by Opponent in EP 2442821 (D12a from EP 2442821 Opposition) and English translation filed by Applicant in U.S. Appl. No. 13/378,778 on Aug. 24, 2012 (D12b from EP 2442821 Opposition).
Grounds of Opposition to European Patent No. EP 2442821 filed on Mar. 3, 2018, by Ferring B.V. (62 pages).
Hashim et al., (2008, "Desmopressin for the treatment of adult nocturia," *Therapy*, 5:667-683 (D27 in EP 2442821 Opposition).
Ilium L., (2002), "Nasal Drug Deliver: New Developments and Strategies," DDT, 7(23):1184-1189, 2002 (D5 from EP 2442821 Opposition).
Kaminetsky et al., (2018),"Efficacy and Safety of SER120 Nasal Spray in Nocturia Patients Pooled Analysis of 2 Randomized, Double-Blind, Placebo-Controlled Phase 3 Trials," *J. Urology*, S0022-5347(18)42971-0; doi: 10.10161j.juro.2018.04.050. (D28 in EP 2442821 Opposition).
Label for Nocdurna, Jun. 2018 (D34 from EP 2442821 Opposition).
Label for Noctiva, Mar. 2017 (D11 from EP 2442821 Opposition).
Lansley, A. B., et al., (2001) Chapter 9, Nasal Drug Delivery, In: Drug Delivery and Targeting, Eds.: Hillery, A.M., et al., Taylor & Francis, pp. 215-243 (D4 from EP 2442821 Opposition).
Lefebvre, A.H., (1989) "Chapter 4, Atomizers," In *Atomization and Sprays*, Hemisphere Publ. Corp., pp. 105-127 (D3 from EP 2442821 Opposition).
Makidon, P.E., et al., (2010) "Characterization of Stability and Nasal Delivery Systems for Immunization with Nanoemulsion-Based Vaccines," J. Aerosol Med. Pulm. Drug. Dev., 23(2):77-89 (D21 in EP2442821 Opposition).
Malmsten, M., (1999) "Chapter 25: Microemulsions in Pharmaceuticals," in Handbook of Microemulsion Science and Technology, Eds.: Kumar, P., et al., Marcel Dekker, Inc., pp. 755-770 (D20 in EP2442821 Opposition).
Management Forum, Program of Conference on Nasal Drug Delivery, 1 & 2 Apr. 2009, London, UK (9 pages) and hand out from Dr. Degenhard Marx, for Presentation N4-8009, "CPS Nasal, New generation of nasal spray systems," (13 pages) (D17a in EP2442821 Opposition).
Marx et al., (2015), "Intranasal Drug Administration-An Attractive Delivery Route for Some Drugs," Drug Discovery and Development Omboon Vallisuta and Suleiman Olimat, IntechOpen, DOI: 10.5772/59468. Available from: https://www.intechopen.com/books/drug-discovery-and-development-from-molecules-to-medicine/intranasal-drug-administration-an-attractive-delivery-route-for-some-drugs (22 pages; D32 in EP 2442821 Opposition).
Marx, D., "CPS nasal, New generation of nasal spray systems," Presentation given at the Annual International Conference of Nasal Drug Delivery, Apr. 24, 2009, London, UK (23 page)(D17 in EP 2442821 Opposition).
Marx, D., (Jul./Aug. 2009), "A Proactive Approach to Developing the Cartridge Pump System (CPS) in a Pressurized Market Environment," *Drug Delivery Techn.*, 9(7):28, 30-33 (D17b in EP2442821 Opposition).
Minutes of the Oral Proceedings (including Annex) for EP 2442821 dated Nov. 28, 2016, for 2442821 Submission of Patentee for EP 2381923 dated Sep. 15, 2017 (D26 in EP2442821 Opposition).
Reddy et al., (2006) "In vivo targeting of dendritic cells in lymph nodes with poly(propylene sulfide) nanoparticles," *J. Controlled Release*, 112:26-34 (D30 from EP 2442821 Opposition).
Response filed Aug. 7, 2018, by Serenity Pharmaceuticals LLC to Notice of Opposition in European Patent No. 2442821 (65 pages).
Response to Office Action and Rule 132 Declaration filed in U.S. Appl. No. 13/378,778 dated Jul. 5, 2016 (D10 from EP 2442821 Opposition).
"Section VI: Liquid Dosage Forms," in *Ansel's Pharmaceutical Dosage Forms and Drug Delivery Systems*, 8th Ed., Eds.: Allen Jr., L. V., et al., Lippincott, Williams & Wilkins, pp. 404-408 and 563, 2005 (D7 from EP 2442821 Opposition).
"Single Ascending Dose Pharmacokinetics of a Low Dose Nasal Spray Formulation of Desmopressin in Healthy Male and Female Subjects," Jul. 8, 2010 (48 pages; D33 from EP 2442821 Opposition).
Stote, R. W., et al., (Oct. 2007) "Intranasal Insulin—A Potential New Treatment Modality for Diabetes Mellitus," *Drug Development Delivery*, 7:86-90, 92 (D14 in EP 2442821 Opposition).
Submission of Patentee for EP 2381923 dated Sep. 15, 2017 (D24 in EP2442821 Opposition).
Submission of Patentee for EP 2442821 dated Sep. 12, 2016 (D25 in EP2442821 Opposition).
Suman, J.D., et al., (2002), "Validity of in vitro tests on aqueous spray pumps as surrogates for nasal deposition," *Pharmaceutical Res.*, 19: 1-6 (D23 in EP2442821 Opposition).
"Bentley Receives Broad U.S. Patent Protection for Its Intranasal Drug Delivery Technology" Jul. 19, 2007, Businesswire (2 pages; D6 from EP 2442821 Opposition).
Pennington et al., (2008), "Spray Pattern and Droplet Size Analyses for High Shear Viscosity Determination of Aqueous Suspension Corticosteroid Nasal Sprays," *Drug. Dev. Ind. Pharm.*, 24:923-929.
Guo et al., (2006), "The Influence of Actuation Parameters on in Vitro Testing of Nasal Spray Products," *J. Pharm. Sci.*, 95:2029-2040.

(56) References Cited

OTHER PUBLICATIONS

U.S. Appl. No. 61/139,871, filed Dec. 22, 2018 (D2 from EP 2442821 Opposition).
Preliminary Opinion of the Opposition Division of the European Patent Office in Opposition of European Patent No. 2381923 (European Patent Application No. 09796558.6) dated Jan. 24, 2020 (14 pages).
Excerpt from "A Randomized . . . Crossover Pharmacokinetic Study of NOCTIVA™ Comparing Systemic Exposure of Two Sprays of 0.83 mcg and One Spray of 1.66 mcg in Normal Healthy Subjects," Aug. 2018 and Declaration from Dr. Samuel Herschkowitz regarding same (Reference D37 and D37a from EP 2442821 Opposition; 22 pages).
Information for Healthcare Professional—Desmopressin Acetate (marketed as DDAVP Nasal Spray, DDAVP Rhinal Tube, DDAVP, DDVP, Minirin, and Stimate Nasal Spray); Center for Drug Evaluation and Research, USFDA (Dec. 4, 2007; 3 pages; D29 from EP 2381923 Opposition).
Submission to European Patent Office by Proprietor Serenity Pharmaceuticals LLC dated Nov. 16, 2018, in Opposition of European Patent No. 2442821 (3 pages).
Preliminary Non-Binding Opinion of the Opposition Division dated Nov. 29, 2018, in Opposition of European Patent No. 2442821 (27 pages).
Reply dated May 2, 2019 by Opponent Ferring BV to Preliminary Non-Binding Opinion of the Opposition Division in Opposition of European Patent No. 2442821 (22 pages).
Reply dated May 2, 2019 by Proprietor Serenity Pharmaceuticals LLC to Preliminary Non-Binding Opinion of the Opposition Division in Opposition of European Patent No. 2442821 (39 pages).
European Patent Office Minutes of Oral Proceedings dated Aug. 30, 2019, in Opposition of European Patent No. 2442821 (4 pages).
European Patent Office Information on Oral Proceedings dated Jul. 2, 2019, in Opposition of European Patent No. 2442821 (15 pages).
Decision of the European Patent Office Opposition Division dated Aug. 30, 2019, Revoking European Patent No. 2442821 (36 pages).
Notice of Opposition filed by Ferring BV dated May 1, 2019, in European Patent No. 2381923 (100 pages).
Patentee's Submission dated Jul. 5, 2016, to the U.S. Patent and Trademark Office in U.S. Pat. No. 9,539,302, including attached declarations of Seymour Fein and Wendy Murray (26 pages; Reference D14 in EP 2381923 Opposition).
Day (2009) "Chapter 13: Aqueous Nasal Dosage Forms in Pharmaceutical, Preformulation and Formulation, Ed: M. Gibson, CRC Press." (19 pages; Reference D18 in EP 2381923 Opposition).
Section VI "Liquid Dosage Forms" from Ansel's Pharmaceutical Dosage Forms and Drug Delivery Systems, Eds. LV. Allen Jr et al., Lippincott Williams and Wilkins, 2005, pp. 404-408 and 563 (7 pages; Reference 219 in EP 2381923 Opposition).
Observations of Proprietor Serenity Pharmaceuticals LLC filed Sep. 26, 2019, in Response to Ferring BV's Notice of Opposition in European Patent No. 2381923 (42 pages).
Experimental Report and Declaration of Seymour Fein, M.D. filed in Opposition Proceedings for EP 2381293 dated Sep. 26, 2019 (3 pages; Reference D30 in EP2381923 Opposition).
Excerpt from "A Randomized . . . Crossover Pharmacokinetic Study of NOCTIVA™ Comparing Systemic Exposure of Two Sprays of 0.83 mcg and One Spray of 1.66 mcg in Normal Healthy Subjects," Aug. 2018 and Declaration from Dr. Seymour Fein regarding same (Reference D27 and D28 from EP 2381923 Opposition; 22 pages).
Notice of Appeal Against Decision of the Opposition Division in EP2442821 filed by Ferring BV in the European Patent Office dated Nov. 7, 2019 (4 pages).
Withdrawal of Appeal Against Decision of the Opposition Division in EP2442821 filed by Ferring BV in the European Patent Office dated Jan. 6, 2020 (3 pages).
Grounds of Appeal Against Decision of the Opposition Division in EP2442821 filed by Serenity Pharmaceuticals LLC in the European Patent Office dated Jan. 9, 2020 (52 pages).

Reply by Ferring BV to Serenity Pharmaceuticals LLC's Grounds of Appeal Against Decision of the Opposition Division in EP2442821 filed in the European Patent Office dated May 4, 2020 (24 pages).
Reply by Ferring BV to Serenity Pharmaceuticals LLC's Observations in Opposition of EP2381923 filed in the European Patent Office dated Dec. 5, 2019 (32 pages).
Chapter 13: Aqueous Nasal Dosage Forms, Nigel Day, in Pharmaceutical Preformulation and Formulation, editor M. Gibson, 2002 (D18a in Opposition of EP2381923).
Chapter 14: Disperse Systems, in Ansel's Pharmaceutical Dosage Forms and Drug Delivery Systems, editor Allen, Jr, L.V. et al, 2005, pp. 385-442 (D19a in Opposition of EP2381923).
Handbook of Chemistry and Physics, pp. F-41 and F-43, 1975 (D32 in Opposition of EP2381923).
U.S. Patent and Trademark Office Patent Trial and Appeal Board's Decision in U.S. Appl. No. 13/141,590, dated Apr. 17, 2019 (15 pages).
"FDA Approves First Treatment for Frequent Urination at Night Due to Overproduction of Urine," U.S. Food and Drug Administration New Release dated Mar. 3, 2017 (2 pages).
Communication pursuant to Article 94(3)EPC issued in EP 2442821 dated Jul. 15, 2015 (4 pages; D32 in Opposition of EP3278809).
European Medicines Agency (EMEA) "ICH Topic E 4: Dose Response Information to Support Drug Registration," Nov. 1994 (10 pages; D33 in Opposition of EP2381923).
European Patent Office's Consolidated List of Citations in Opposition of EP2381923 dated Sep. 9, 2020 (3 pages).
European Search Report for 10790053.2, dated Jul. 7, 2013. 6 pages.
International Search Report for International Patent Application No. PCT/US2009/068962, dated Nov. 19, 2010, (4 pages).
Minutes of the Oral Proceedings in European Patent Office Appeal No. J0004/17 dated May 16, 2018 (4 pages; D35 in Opposition of EP2381923).
Minutes of the Oral Proceedings of the Examining Division in EP2442821 dated Nov. 28, 2016 (13 pages; D26 in Opposition of EP3278809).
NDA Approval from U.S. Food and Drug Administration to Serenity Pharmaceuticals regarding Noctiva (NDA201565) dated Mar. 3, 2017 (5 pages).
Notice of Opposition filed by Ferring AB against European Patent No. 3278809 dated Aug. 20, 2020 (92 pages).
Ozsoy et al., "Nasal Delivery of High Molecular Weight Drugs," Molecules, 2009, 14:3754-3779.
Sharma et al., "Permeation Enhancers in the transmucosal delivery of macromolecules," Pharmazie, 2006, 61:495-504.
Summons to Oral Proceedings issued by the Examining Division in EP2442821 dated May 31, 2016 (5 pages; D30 in Opposition of EP3278809).
U.S. Food & Drug Administration Summary Review for Regulatory Action for Noctiva (Desmopressin Acetate Nasal Spray) signed Mar. 3, 2017 (22 pages; D33 in Opposition of EP3278809; D34 in Opposition EP2381923).
WebMD Health News by Miranda Hitti, "2 Deaths Spur Bed-Wetting Drug Warning: FDA Warns that Some Patients Taking Desmopressin May Be at Risk of Seizure and Death," Dec. 4, 2007 (3 pages).
Written Opinion of the International Searching Authority (ISA/EP) for International Patent Application No. PCT/US2009/068962, dated Nov. 19, 2010, (9 pages).
Written Submission of Ferring AB in advance of Oral Proceedings dated Aug. 19, 2020, in Opposition of EP2381923 (26 pages).
Written Submission of Serenity Pharmaceuticals, Inc. in advance of Oral Proceedings dated Aug. 19, 2020, in Opposition of EP2381923 (6 pages).
Observations of Serenity Pharmaceuticals LLC filed Jan. 11, 2021, in Opposition to EP Patent No. 3278809 (128 pages).
Written Submission of Opponent Ferring BV dated Apr. 29, 2021, submitted in advance of Oral Proceedings in Opposition of EP Patent No. 2381923 (17 pages).

(56) References Cited

OTHER PUBLICATIONS

Written Submission of Patentee Serenity Pharmaceuticals LLC dated Apr. 30, 2021, including Declaration of James Longstreth, PhD, submitted in advance of Oral Proceedings in Opposition of EP Patent No. 2381923 (16 pages).
Levine, Chapter 4 "How Drugs Reach Their Site of Action" in Pharmacology Drug Actions and Reactions, Little Brown, Boston, MA, 1974, pp. 49-63.
Letter from Opponent Ferring BV dated Jun. 11, 2021, Requesting Entry of Declaration of Dr. Kristian Juul, filed Jun. 11, 2021, in Opposition of European Patent No. 2381923 (20 pages) including: Declaration of Kristian Juul dated Jun. 7, 2021, filed Jun. 11, 2021, by Opponent Ferring BV in Opposition of European Patent No. 2381923, Annex 1 to Declaration of Kristian Juul—Curriculum Vitae of Kristian Juul, and Annex 2 to Declaration of Kristian Juul—Juul et al., 2013, "Temporal Delays and Individual Variation In Antidiuretic Response to Desmopressin," *Am. J. Renal Physiol.*, 304:F268-F278.
Information about the Result of Oral Proceedings on Jul. 1, 2021, in Opposition of European Patent No. 2381923 dated Jul. 6, 2021 (1 page).
Letter from Patent Proprietor Serenity Pharmaceuticals LLC dated Jun. 21, 2021, Regarding Oral Proceedings Scheduled for Jul. 1, 2021, in Opposition of European Patent No. 2381923 (4 pages).
Summons to Attend Oral Proceedings dated Jun. 29, 2021, including Preliminary Non-binding Opinion of the European Patent Office Opposition Division in Opposition of European Patent No. EP3278809 (99 pages).
Response by Opponent Ferring BV dated Apr. 22, 2021, to Patent Proprietor Serenity Pharmaceuticals Observations in Opposition of European Patent No. EP3278809 (56 pages).
Reference D45 in Opposition of European Patent No. 3278809—Declaration of Attorney Thimming on Information Disclosure Statement of Patentee Serenity Pharmaceuticals filed in U.S. Pat. No. 9,539,302 (21 pages).
Reference D44 in Opposition of European Patent No. 3278809—Communication from European Patent Office in Divisional Application No. EP 3437633 dated Jul. 9, 2020 (4 pages).
Intranasal Desmopressin Administration, U.S. Appl. No. 17/330,798, filed May 26, 2021.
Decision dated Feb. 8, 2022, of the European Patent Office Revoking European Patent No. EP3278809 (2 pages).
Interlocutory Decision of the European Patent Office dated Nov. 25, 2021, in Opposition of European Patent No. EP2381923 (Serenity Pharmaceuticals LLC, patentee; 46 pages).
Letter from Patentee Serenity Pharmaceuticals LLC to the European Patent Office dated Oct. 21, 2021, in Opposition of European Patent No. EP3278809 (3 pages).
Letter from Patentee Serenity Pharmaceuticals LLC to the European Patent Office dated Dec. 6, 2021, in Opposition of European Patent No. EP3278809 (10 pages).
Letter from Patentee Serenity Pharmaceuticals LLC to the European Patent Office dated Feb. 3, 2022, Requesting Revocation of European Patent No. EP3278809 (3 pages).
Letter from Opponent Ferring BV to the European Patent Office dated Nov. 2, 2021, in Opposition of European Patent No. EP3278809 (Serenity Pharmaceuticals LLC, patentee; 3 pages).
Minutes of the Oral Proceedings of the European Patent Office held Jul. 1, 2021, in Opposition of European Patent No. EP2381923 (Serenity Pharmaceuticals LLC, patentee; 10 pages).
Notice of Appeal by Opponent Ferring BV dated Feb. 1, 2022, in Opposition of European Patent No. EP2381923 (Serenity Pharmaceuticals LLC, patentee; 4 pages).
Grounds of Appeal dated Apr. 4, 2022, filed by Opponent and Appellant Ferring BV in Appeal of Decision in Opposition of European Patent No. EP2381923 (42 pages).
Minutes of Oral Proceedings from the European Patent Office Boards of Appeal in the Opposition of EP2442821 (Patent Proprietor: Serenity Pharmaceuticals LLC, Opponent: Ferring BV) dated May 31, 2022 (4 pages).
Communication of Termination of Opposition Proceedings in EP 3278809 dated May 24, 2022, from the European Patent Office (Patent Proprietor: Serenity Pharmaceuticals LLC, Opponent: Ferring BV) (1 page).
Communication of the Preliminary Opinion of the Board of Appeal in the Opposition of EP2442821 (Patent Proprietor: Serenity Pharmaceuticals LLC, Opponent: Ferring BV) dated Mar. 9, 2022 (10 pages).
Intranasal Desmopressin Administration, U.S. Appl. No. 17/330,798, filed May 6, 2021.

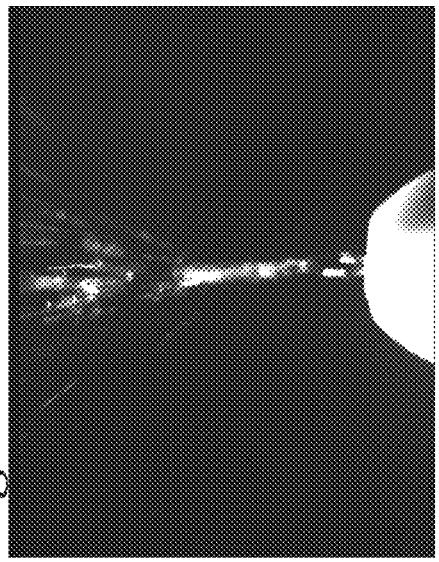
Figure 3C
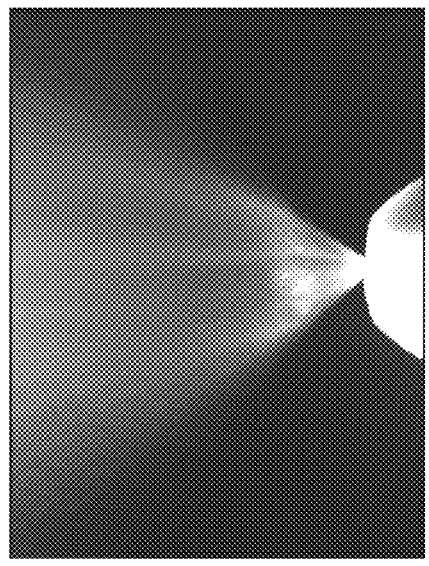
Figure 3D
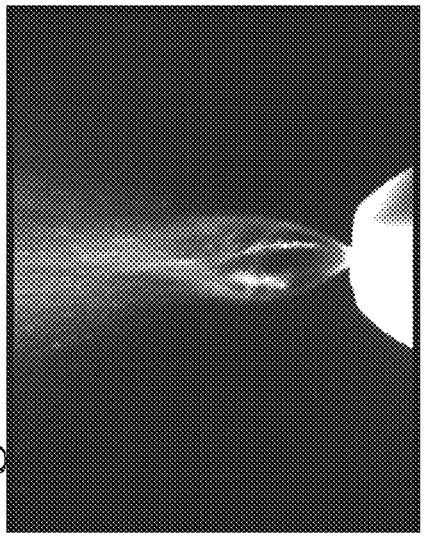
Figure 3A
Figure 3B

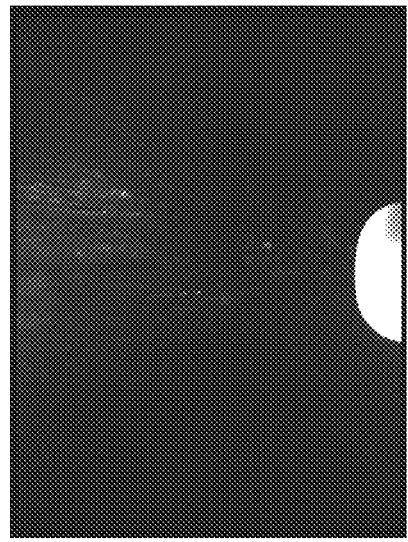
Figure 4B
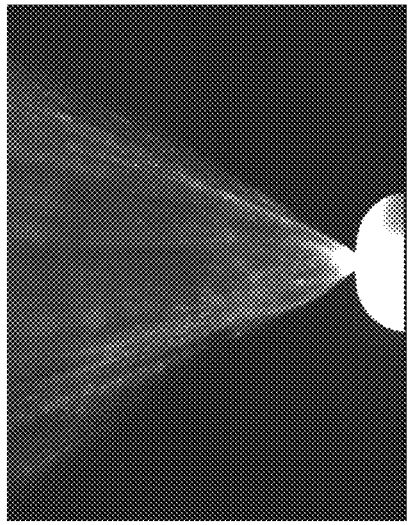
Figure 4D
Figure 4A
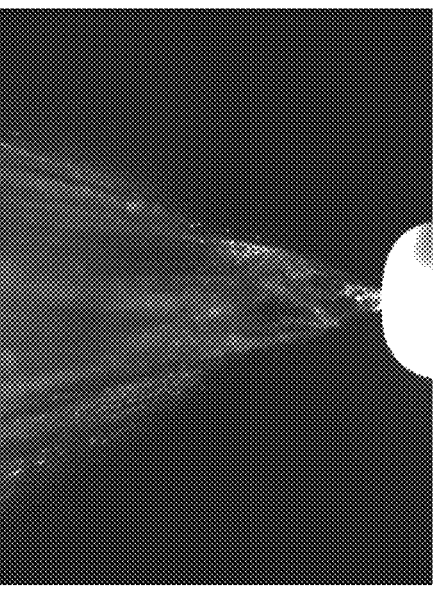
Figure 4C

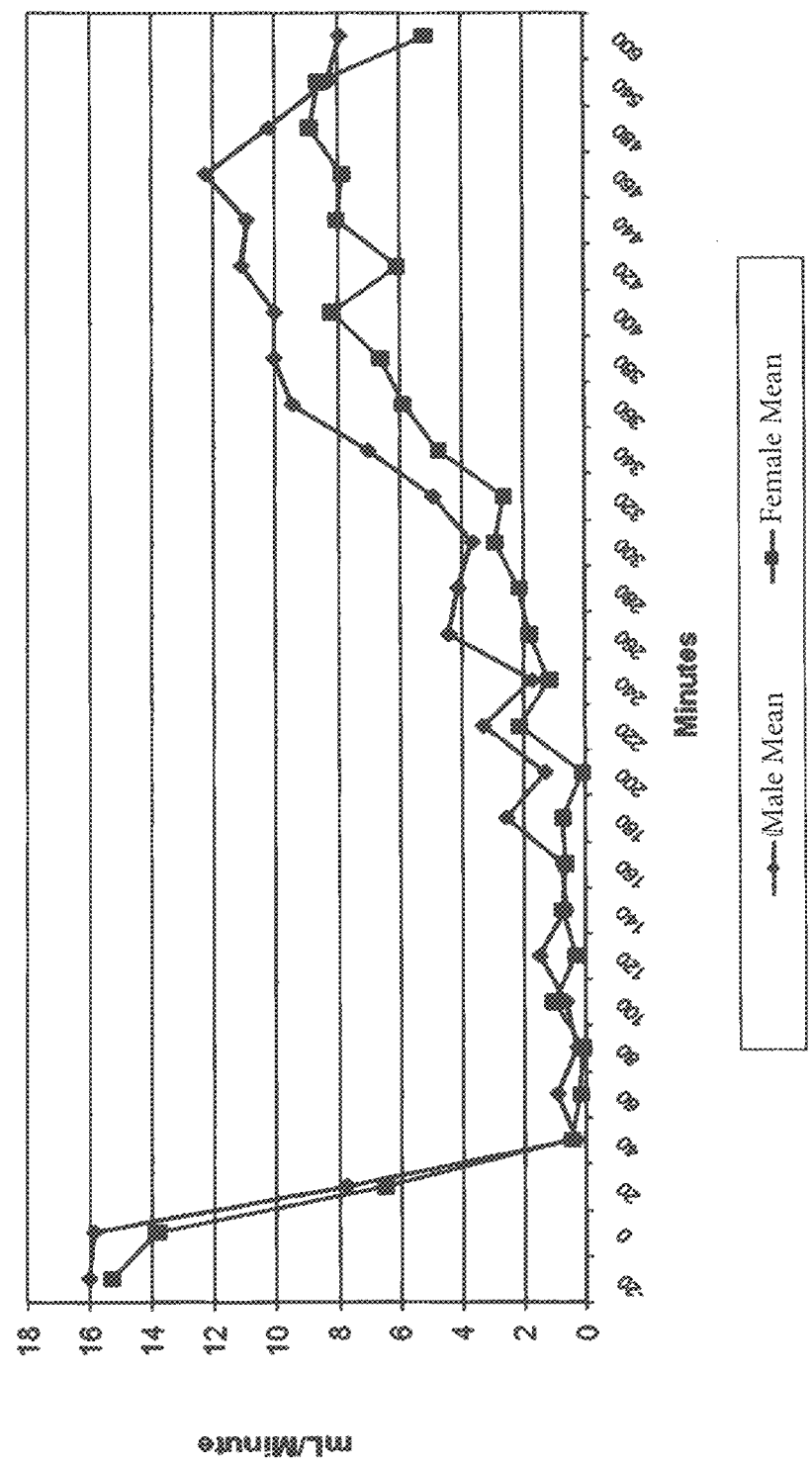

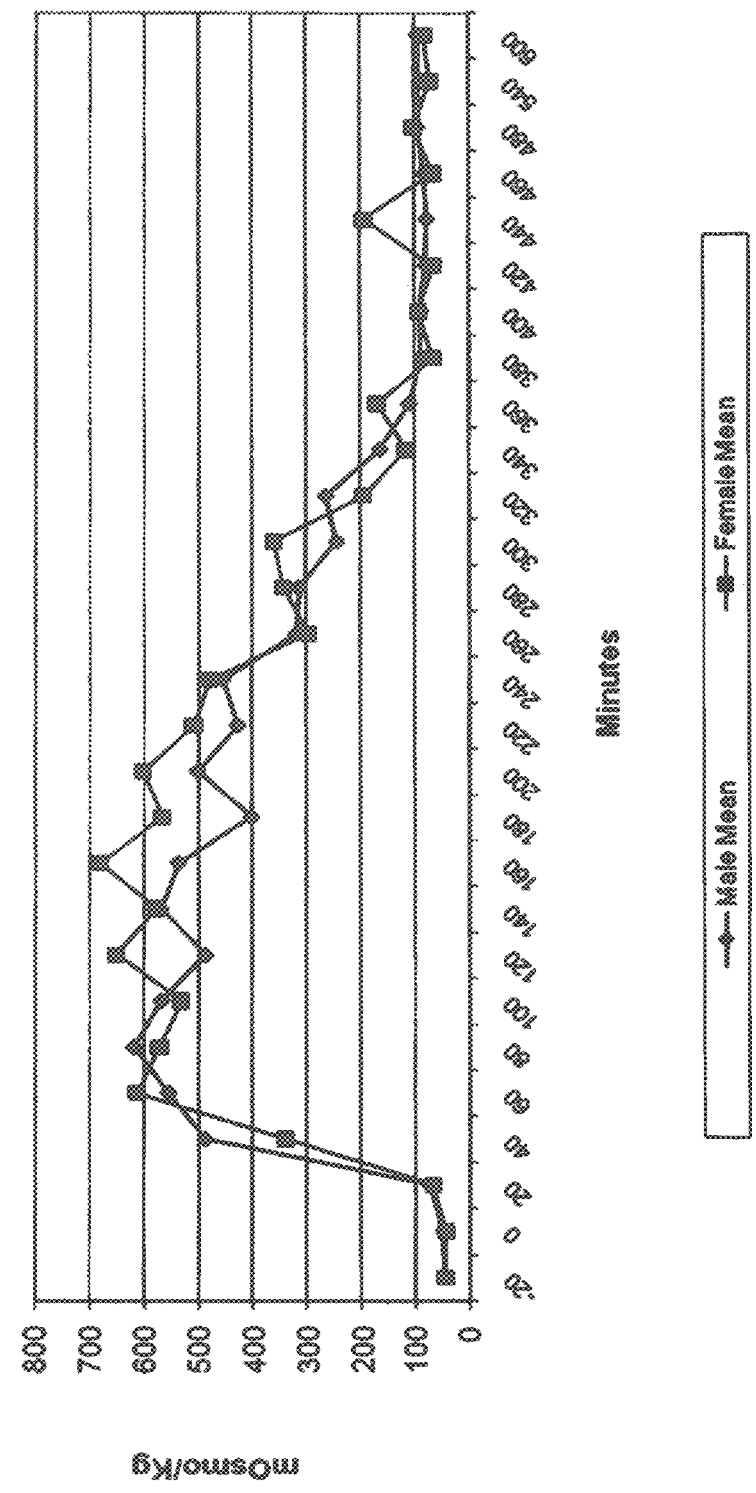

SAFE DESMOPRESSIN ADMINISTRATION

REFERENCE TO RELATED APPLICATION

This application is a Divisional of Ser. No. 13/378,778, filed Mar. 5, 2012, now U.S. Pat. No. 9,539,302, which is a National Stage filing under 35 U.S.C. Section 371 of PCT/US2010/038663, filed Jun. 15, 2010, which claims the benefit of an priority to U.S. Provisional Application No. 61/268,954, filed Jun. 18, 2009, the complete disclosure of which is hereby incorporated by reference.

FIELD OF THE INVENTION

The invention relates to compositions and devices for intranasal administration of desmopressin so as to induce antidiuretic effects such as voiding postponement in a patient while minimizing the likelihood that the patient suffers from hyponatremia.

BACKGROUND OF THE INVENTION

Desmopressin (1-desamino-8-D-arginine vasopressin, dDAVP®) is an analogue of vasopressin. Desmopressin has decreased vasopressor activity and increased anti-diuretic activity compared to vasopressin, and, unlike vasopressin, does not adversely affect blood pressure regulation. This enables desmopressin to be used clinically for anti-diuresis without causing significant increases in blood pressure. Desmopressin is commercially available as the acetate salt and is commonly prescribed for primary nocturnal enuresis (PNE) and central diabetes insipidus.

Desmopressin is a small peptide and is characterized by poor bioavailability. For treatment of severe illness such as cranial diabetes insipidus, it may be administered intravenously or subcutaneously, routes which essentially are 100% bioavailable. When taken in the commercialized dose forms of oral, sublingual and nasal spray delivery, bioavailability is poor. Oral doses (pills) have a bioavailability far less than one percent, produce a wide range of blood concentrations of the drug depending on many factors, and produce a generally indeterminate duration of antidiuretic effect. Administration of desmopressin via the buccal mucosa and trans dermally also have been suggested. Intranasal dosage forms have been approved for treatment of PNE, but the commercially available product (Minirin™) has now been declared to be unsafe for this use.

Hyponatremia is a condition in which the sodium concentration in the plasma is too low, e.g. below about 135 mmol/L. Severe hyponatremia can result in electrolyte abnormalities that can cause cardiac arrhythmias, heart attack, seizures or stroke. A hyponatremic state in patients administered desmopressin therapy occurs when the water channels in the kidneys of the patient are activated by the drug and the patient consumes aqueous liquids. This can but does not always result in lowering of blood osmolarity, lowering of sodium concentration, and consequent neurological damage. Some patients on a desmopressin regimen exhibit hyponatremia suddenly after having taken the drug without incident for long periods. Others develop the condition very early in the therapeutic regime. In short, the incidence of hyponatremia has largely been regarded as a stochastic side effect of the antidiuretic desmopressin therapy, avoidable only by avoidance of fluid intake while under the drug's effect.

Recent deaths from hyponatremia have been attributed to over intake of water while under the influence of desmopressin. As a result of these experiences, the U.S. Food & Drug Administration recently has warned physicians that use of desmopres sin should be curtailed, that it is no longer indicated as appropriate for certain conditions, such as primary nocturnal enuresis (PNE), and has "Black Boxed" the drug. The recent warning stated that "[c]ertain patients, including children treated with the intranasal formulation of [desmopressin acetate] for primary nocturnal enuresis (PNE), are at risk for developing severe hyponatremia that can result in seizures or death."

Currently, approved labeling for desmopressin administered intranasally for treatment of PNE indicates bioavailability in the formulation is 3-5% and recommends dosing 10-40 micrograms per day. The average maximum plasma/serum concentrations achieved ($C_{max}$) with a typical intranasal dose (20 µg, 10 µg in each nostril) of desmopressin for PNE is at least approximately 20-30 pg/ml, based on 3-5% bioavailability with a 6 to 10 fold range. While existing formulations of desmopressin have proven to be adequate for many patients when used for these clinical indications, variable efficacy and occasional hyponatremic episodes continue to be problems related to the aforementioned variability.

U.S. Pat. No. 7,405,203 discloses antidiuretic therapy methods and desmopressin dosage forms. It discloses that the threshold plasma concentration for activation of the antidiuretic effect of desmopressin in humans is very low, less than about 1.0 pg/ml, and based in part on this observation, proposes the use and teaches how to make and use novel low dose desmopressin dosage forms that can substantially avoid the stochastic and unpredictable onset of hyponatremia. This is accomplished by administration of a very low dose of the drug, a dose sufficient to raise the desmopressin concentration in the blood only slightly above its threshold (e.g., about 0.5 pg/ml) from about 1.0, to about 10, and perhaps as high as 15 pg drug per ml of blood in some patients, but preferably no greater than about 10 pg/ml. This low concentration was discovered to be sufficient to induce potent antidiuretic effects of limited and controlled duration. Thus, the low blood concentration in combination with the known, approximate 90+ minute half life of desmopressin in a healthy person can function to control the "off switch" of the drug's activity and thereby to limit the duration of antidiuresis. This very significantly reduces the likelihood that the patient will drink sufficient liquids during the interval the drug is physiologically active such that the patient's homeostasis mechanisms are overwhelmed and blood sodium concentration falls to dangerous levels.

For example, in the treatment of nocturia (awakening from sleep to void at night) a low dose producing, e.g., a blood concentration of 5-7 pg/ml, can be administered at bed time. In less than about one half hour, desmopressin concentration is at its maximum of about 7 pg/ml, and urine production is suppressed. After two hours (one half life) the desmopres sin concentration falls to about 3.5 pg/ml, at 3.5 hr (second half life), concentration is about 1.75, at 5 hr, approximately 0.85, and at 6 hours the concentration has fallen below the activation threshold (in many patients about 0.5 pg/ml) and the patient is making urine normally. If he retires at 11:00 PM, during the first six hours the patient makes little or no urine, his bladder is essentially empty, and his urge to urinate is accordingly suppressed. By 5 AM or so, urine production is restored and in an hour or two the patient wakes to urinate. As another example, a small dose, say 2-3 pg/ml administered intranasally or through a trans or intradermal patch, can induce safe antidiuresis for about three hours before normal urine production is restored.

Intranasal administration is an attractive dosage route, and if one could formulate an intranasal dosage form that would consistently produce a desmopressin blood concentration within or near the desired low dose range disclosed in the '203 patent, the incidence of the hyponatremia side effect would be reduced or eliminated, and the drug could be used safely as a convenience, as well as for the management of serious and bothersome conditions. While it clearly is within the skill of the art to produce a low dose intranasal desmopressin formulation that will be serviceable and induce safe antidiuresis reproducibly, the ideal intranasal dose form would, from one administration to the next, and from batch to batch, consistently produce a blood concentration within a relatively narrow target blood concentration range. It also would be desirable to formulate such a product so as to minimize the chances of abuse (multiple dosing) that could lead to antidiuresis of longer duration and potentially the development of hyponatremia. Because of variability in the human nasal mucosa, its permeability, the small amount of active peptide per dose, and many physical factors involved in self-administration of an intranasal drug product, the product's bioavailability necessarily varies from person to person and use to use.

SUMMARY OF THE INVENTION

The invention provides a convenient, intranasal desmopressin safety dispenser for inducing in members of a target patient population an antidiuretic effect while reducing the risk that a member of the population may develop hyponatremia. The dispenser comprises a reservoir having disposed therein a composition comprising a preparation of desmopressin and a nasal membrane permeation enhancer in an amount sufficient to constitute multiple drug doses. The reservoir is in communication with an outlet and is fitted with a pump, preferably a disposable pump, and preferably one that can be actuated manually, such as a squeeze bottle actuated dispenser, or a plunger pump fitted onto a glass bottle. The pump enables serially dispensing multiple metered doses from the reservoir through the outlet in the form of a spray into a nostril or nostrils of a patient so as to deposit a dose of consistent size onto an intranasal mucosal or other surface. The pump can include a seal preventing bacterially contained ambient air from entering the dispenser after a dose of desmopressin is released.

Each spray comprises a multiplicity of droplets, preferably with an average volume distribution in the range of 20 μm for D10 to about 300 μm for D90. This means that about 10% of the droplets are smaller than about 20 μm in diameter and 90% are smaller than 300 μm in diameter. Each spray dose is preferably of a weight and desmopressin concentration such that it comprises between 0.5 ng desmopressin per kilogram of the patient's body weight and 75 ng desmopressin per kilogram of the patient's body weight. For example, a spray dose can include between about 0.05 μg and 5.0 μg desmopres sin, depending primarily on the size of the patient and the desired duration of the antidiuretic effect. The spray is characterized by a desmopres sin bioavailability greater than about 5%, that is, between about 5% and 25% of the active in the composition actually enters the patient's bloodstream and contributes to the drug effect, and the remainder is degraded, typically by digestion. Generally, the higher the bioavailability of a spray, the less desmopressin per spray needs to be delivered into a nasal cavity, and vice versa, the goal being to achieve more consistently a target desmopressin maximum blood concentration ($C_{max}$) in members of the patient population.

The droplets of the spray dose form a plume as they are ejected from the nozzle of the dispenser. The droplets are not ejected in a linear stream, but rather form a plume that is generally conical in shape. Furthermore, the droplets are not dispersed uniformly within the plume, but travel primarily near the perimeter of the cone, such that the number of droplets per unit volume in the cone increases in a direction normal to the central axis of the cone. In this way, an axial cross section of the conical volume at a distance such as three centimeters from its apex (at the nozzle of the spray device) preferably describes an annular disk of droplets, with few droplets at the center and a substantial concentration along the perimeter. In most instances, the cross-section of the plume is substantially circular, although a certain degree of ellipticity can of course be tolerated. A desmopressin spray plume in which more of the droplets travel nearer the perimeter of the conical volume promotes contact with intranasal luminal mucosal surfaces and a more predictable bioavailability.

In accordance with the invention, the combination of properties of the spray dispenser and the composition it contains enables respective doses of spray to be effective to restrict the concentration of desmopressin produced in the bloodstream of patients, on a per kilogram basis, to a relatively narrow range, thereby to achieve a relatively consistent, time limited duration of antidiuresis. Stated differently, respective successive spray doses establish in a patient by drug transport across intranasal mucosal membranes a $C_{max}$ of desmopressin which is relatively consistent. The amount of drug delivered to the blood stream for repeated doses from the same dispenser to the same person preferably should differ no more than 100%, and preferably less than 50%. The dispenser's coefficient of variation is similar to the coefficient of variation of $C_{max}$ produced by serial subcutaneous doses of desmopressin designed to achieve the same target $C_{max}$. Preferably, respective successive spray doses are sufficient to establish in a patient by intranasal delivery a $C_{max}$ of desmopressin having a coefficient of variation within about 50%, more preferably about 25%, of the coefficient of variation of $C_{max}$ produced by a subcutaneous dose of desmopressin designed to achieve the same target $C_{max}$.

This consistency of bioavailability also is reflected in another property of dispensers of the invention, namely, they serve to establish in a patient by drug transport across intranasal mucosal membranes delivery of blood concentrations of desmopressin substantially directly proportional to the mass of desmopressin dispensed into the nostril(s) of a said patient. This permits self titration of the length of antidiuresis desired by a patient. Generally, the desmopressin $C_{max}$ is directly proportional to the amount of nasally administered desmopressin over a $C_{max}$ ranging from about 0.5 pg/ml to about 10.0 pg/ml.

The value of the target $C_{max}$ may be varied, depending on the duration of the antidiuretic interval the dispensed composition is designed to induce. For example, a product designed for a 7-8 hour interval of urine production suppression might be designed to deliver a $C_{max}$ of no more than 15+/−3 pg/ml. Thus, by way of illustration, a 7 hour product designed for children might have a bioavailability of 20% and a desmopressin load per spray of 0.75 μg or 750 ng. This would mean that about 150 ng of drug would reach the patient's blood stream, and that a 33 kg (~75 lb.) child would achieve the target $C_{max}$ of about 15 pg/ml. Another embodiment of the same product might have a bioavailability of 10% and a desmopressin load per spray of 1.5 μg or 1500 ng, again producing about 150 ng drug in the patient's bloodstream and the target $C_{max}$ of about 15 pg/ml. Another exemplary product may be designed for a 3-4 hour urine interruption and might deliver a $C_{max}$ of no more than about 3 pg/ml. Such a product, designed, for example, for use by women averaging 60 kg (~130 lb.), might be 25% bioavailable and comprise a 250 ng desmopressin load per spray, or 15% bioavailable with a 350 ng load. In both cases, the bioavailable dose would be about 50 ng desmopressin, and the $C_{max}$ about 3 pg/ml.

Alternatively, a single dispenser which delivers, e.g., 200 ng or 500 ng per spray, when used in accordance with package insert or physician instructions, may serve to achieve, for example, different durations of antidiuresis in the same person or the same duration of antidiuresis in a 75 kg child or 150 kg adult, simply by varying the number of spays delivered per administration event. Typically, about 20 minutes after administration of the pharmaceutical composition of the present invention, the mean urine output per minute in a treated individual decreases to less than about 4 ml/minute, preferably less than about 1 ml/min, and stays in this low range for a desired time period, such as 180 minutes, 240 minutes, 300 minutes, 360 minutes, or 420 minutes. About twenty minutes after administration, the mean urine osmolarity is greater than about 300 mOsmol/kg and remains at high concentration for a period of time ranging up to 180 minutes, 240 minutes, 300 minutes, 360 minutes, or 420 minutes.

A primary and important property of the dosage forms of the invention is that they consistently deliver per spray a maximum blood concentration within a relatively narrow time and dose range, and therefore avoid or minimize accidental delivery of a larger dose resulting in a longer than expected antidiuretic effect and the possibility of induction of hyponatremia. Consistent delivery, as the phrase is used herein, should be taken to mean repeatable within a range similar to the range observed when administering very low doses of desmopressin by subcutaneous injection, or perhaps somewhat greater. Such consistency generally is achieved more easily exploiting formulations with higher bioavailability, and accordingly a bioavailability of at least 5%, preferably at least 10%, more preferably at least 15%, and preferably even higher is preferred. Higher bioavailability is achieved by exploiting formulation technology, especially the use of permeation enhancers, and by chemical engineering of the spray composition as disclosed herein.

In one embodiment, the dispenser may further comprise means for blocking dispensing of a second desmopressin spray, or series of sprays above a certain dose, e.g., above about a dose sufficient to produce a blood concentration above about 10 to 12 pg/ml, for a predetermined time interval after dispensing a first dose. This can be achieved passively as a consequence of the design of the spray mechanism as disclosed, for example, in U.S. Pat. No. 7,335,186, the disclosure of which is incorporated herein by reference. Alternatively, an active timer, powered by a battery, mechanical spring, or compressed gas within the dispenser, may be included together with mechanisms known per se designed to preclude a second dispensing until passage of a predetermined interval, e.g., 8 hours, or somewhere between 6 to 24 hours. Such a mechanism can discourage abuse of the product and further minimize the chances that a patient may inadvertently or intentionally self-induce antidiuresis for too long.

In various embodiments, the dispenser may be formulated to induce antidiuresis in a target patient population for less than six hours, for between 2 and 4 hours, or for between 4 and 7 hours. Maintaining the antidiuretic state for more than about 8 hours is not recommended. The target patient population may be, for example, children, children weighing less than 35 kg, children weighing between 35 and 50 kg, adult females, females weighing between 50 and 75 kg, adult males, males weighing between 70 and 85 kg, or males weighing more than 85 kg.

In addition to providing desmopressin safety dispensers, the invention also provides the spray plumes for delivering desmopressin to intranasal luminal mucosal surfaces. Each plume is a composition of matter that includes an intranasal desmopressin dose in the form a plume, preferably ejected over a time interval from the nozzle of a metered dose spray device. The plume includes a volume of moving droplets which together define a conical volume having a central axis and an apex at the nozzle of the spray device, such that an axial cross section of the conical volume at a surface about 3 centimeters or less from the apex preferably describes an annular disk of droplets. The droplet density within the conical volume increases in a direction normal to the axis. The droplets that form the plume over the time interval eventually include between about 0.05 µg and 5.0 µg of desmopressin, although it is not required that the complete dose be in the plume at any particular instant in time. The droplets of the plume are preferably formed of an oil-in-water emulsion; may include one or more permeation enhancers; and are optionally free of preservatives.

The currently preferred permeation enhancers for use in the formulation are "Hsieh enhancers" (see U.S. Pat. No. 5,023,252) available commercially from CPEX Pharmaceuticals (formerly Bentley) of Exeter, N.H. Preferred within the class of Hsieh enhancers useful in the articles of manufacture of the invention are those disclosed in U.S. Pat. No. 7,112,561 and U.S. Pat. No. 7,112,561, and the currently most preferred are disclosed in U.S. Pat. No. 7,244,703, such as cyclopentadecanolide, known in the trade as CPE-215. Many other enhancers may be used.

The desmopressin plume can be formulated to deliver transmucosally sufficient desmopressin to the bloodstream of a patient to produce a desired peak desmopressin blood concentration (such as a peak blood concentration no greater than 15+/−3 pg/ml, 10+/−3 pg/ml, or 7+/−3 pg/ml). The target patient population (in whom the peak desmopressin blood concentration is to be reached) can include, for example, children weighing 35 kg, adults weighing 70 kg, children weighing less than 35 kg, children weighing between 35 and 50 kg, adult females, adult males, females weighing between 50 and 75 kg, males weighing between 70 and 85 kg, and males weighing more than 85 kg. Depending on the target population, exemplary dose ranges (i.e. the total amount of desmopressin released into the plume over time) can include, between about 0.05 µg and 5.0 µg desmopressin, between about 0.2 µg and 1.0 µg desmopressin about 0.5 µg desmopressin, or about 0.75 µg desmopressin.

The invention further provides methods of inducing an antidiuretic effect in a patient by intranasally administering to the patient a desmopressin plume as described above. These methods permit reliable administration of desmopressin to achieve a safe, effective peak desmopressin concentration in the bloodstream of the patient. Depending on the patient and the desired duration of antidiuresis, target peak desmopressin concentrations can include, for example, 15+/−3 pg/ml, 10+/−3 pg/ml, or 7+/−3 pg/ml of desmopressin in the blood. If desired, methods of the invention can be used to achieve relatively brief periods of antidiuresis, such as a period less than six hours or from two to four hours, or a more extended period, such as between about four and seven hours.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows the nasal spray device before actuation. FIG. 2B shows the formation of a plume by nasal spray device following actuation of the device.

FIGS. 3A-D are a series of photographs of the stages of formation of a traditional spray plume, including formation phase, stable phase and dissolution phase.

FIGS. 4A-D are a series of photographs of the stages of formation of a spray plume of the present invention, including formation phase, stable phase and dissolution phase.

FIG. 8 is a graph of mean urine output vs. time (600 minutes) for men and women treated with 2000 ng intranasally administered desmopressin composition of the invention.

FIG. 9 is a graph of mean urine osmolarity vs. time for men and women treated with the same composition of the invention.

FIGS. 10A-10C show the spray pattern at a height of 3 cm, and FIGS. 10D-10F show the spray pattern at a height of 6 cm.

DESCRIPTION

Figure 1:
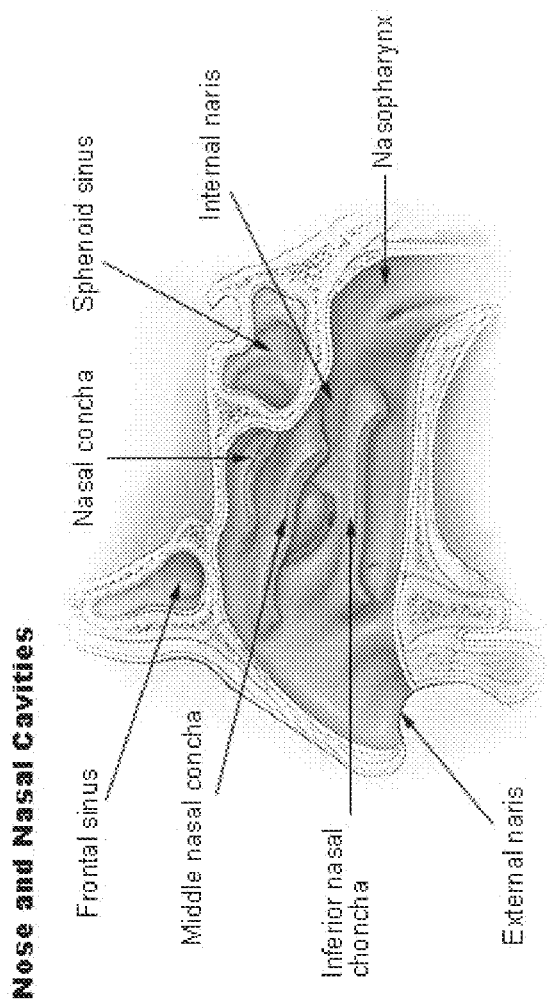
FIG. 1 shows a schematic diagram of the nasal cavity.

The term bioavailability is used to describe the fraction of an administered dose of drug that reaches the systemic circulation. By definition, when a medication is administered intravenously, its bioavailability is 100%. However, when administered via other routes, such as intranasally, bioavailability decreases due to incomplete absorption and other factors. Thus, bioavailability is a measurement of the extent of a therapeutically active drug that reaches the systemic circulation and is available at the site of action. It differs widely depending on chemical and physical properties of the drug in question and its route of administration. A quantity of the composition of the invention administered intranasally refers to the quantity that exits the spray nozzle and enters the nostril(s). A quantity of the composition of the invention delivered refers to the quantity that actually reaches the bloodstream, i.e., becomes bioavailable. Proteins and peptides are relatively large and fragile molecules whose activity generally depends on their tertiary structure. The bioavailability of protein and peptide therapeutics administered other than parenterally is notoriously poor and variable.

The coefficient of variation, $C_v$, as used herein, refers to a number expressed as a percentage that is a measure of the variability of the amount of and rapidity with which active drug gets into the blood stream when the same drug dose form is administered the same way, to the same person over many administrations or to many different persons. A coefficient of variation can be measured for $C_{max}$, $T_{max}$ (time at which $C_{max}$ is achieved), or AUC (area under the curve). It is often expressed as the ratio of the standard deviation of a set of measurements to the mean of those measurements. Generally, intravenous or subcutaneous administration of any drug will have an inherently smaller $C_v$ as compared with transdermal or oral administration. Intranasal administration of desmopres sin is characterized not only by poor bioavailability, but also by a high $C_v$. Thus, the commercially available Minirin® nasal spray product on the basis of $C_{max}$ achieved per nasal spray dose has a high $C_v$, 2 to 2.5 times that of subcutaneous injection. Thus, two patients of the same weight using the same drug ostensibly the same way may experience widely varying blood concentrations of desmopressin, as measured, for example, using $C_{max}$, which may have a range of six to ten fold.

The coefficient of variation is calculated from measured blood concentrations. Accordingly, the imprecision of the analytical technique used to make the measurements comprising the raw data will contribute to $C_v$. An assay with a large inherent error bar will produce a higher measured $C_v$ than an assay with a smaller error bar. When the measurements are made at the lower end of the dynamic range of an assay, where the standard deviation of the measurements is larger, $C_v$ as calculated based on the data will be larger than the $C_v$ of a larger dose of the same drug administered the same way and measured using the same assay.

The term "permeation enhancer," as used herein, refers to one or a mixture of substances which when formulated together with a peptide active, such as desmopressin, have the effect of increasing the fraction of the peptide applied to a nasal mucosal surface that traverses the mucosal membrane and enters the bloodstream, i.e., increases bioavailability. Many such permeation enhancers are known, as described herein. Generally, the addition of a permeation enhancer to a peptide drug formulation designed for intranasal administration will increase the fraction of peptide that reaches the circulation by at least about 25%, preferably at least 50%, and most preferably at least about 100%. Thus, consider two intranasal formulations of identical composition except composition 1 has no enhancer and composition 2 comprises an additional substance. If composition 1, when administered, results in a blood concentration of 50 pg/ml, the substance falls within the definition of an enhancer if composition 2 results in a blood concentration of at least 62.5 pg/ml (25% improvement). A preferred permeation enhancer would produce a blood concentration of about 100 pg/ml (100% improvement).

The term "major axis," as used herein, refers to the largest chord that can be drawn within the fitted spray pattern that crosses the pattern in base units (mm).

The term "minor axis," as used herein, refers to the smallest chord that can be drawn within the fitted spray pattern that crosses the pattern in base units (mm).

The term "ellipticity," as used herein, refers to the ratio of the major axis to the minor axis.

The term "$D_{10}$," as used herein, refers to the diameter of droplet for which 10% of the total liquid volume of sample consists of droplets of a smaller diameter (μm).

The term "$D_{50}$," as used herein, refers to the diameter of droplet for which 50% of the total liquid volume of sample consists of droplets of a smaller diameter (μm), also known as the mass median diameter.

The term "$D_{90}$," as used herein, refers to the diameter of droplet for which 90% of the total liquid volume of sample consists of droplets of a smaller diameter (μm).

The term "span," as used herein, refers to measurement of the width of the distribution, in which a smaller value correlates with a narrower distribution.

The term "% RSD," as used herein, refers to the percent relative standard deviation, the standard deviation divided by the mean of the series and multiplied by 100, also known as % $C_V$.

The invention herein provides improvements in desmopressin nasal spray devices characterized by delivering through the nasal mucosal surfaces and into the circulation of a more consistent as well as a lower desmopressin dose so as to induce a predetermined time-limited antidiuretic effect. The nasal spray drug product contains desmopressin and a mucosal permeation enhancer which functions to promote passage of the peptide drug through the nasal mucosa. The active typically is dissolved or suspended in solutions or mixtures of excipients (e.g., preservatives, viscosity modifiers, emulsifiers, buffering agents, etc.) in a pressurized, but preferably non-pressurized, dispenser that delivers a specifically controlled amount of spray containing a metered dose into one or both nostrils. The dose typically is metered by the spray pump, which is typically finger or hand actuated. The nasal spray is designed for discharge of multiple spray doses, e.g., 10 to 100 or more. It may be designed to administer the intended dose with multiple sprays, e.g., two sprays, e.g., one in each nostril, or as a single spray, or to vary the dose in accordance with the weight, sex, or maturity of the patient, or to permit variation by the patient of the duration of antidiuresis.

The object of the design of the safety spray device is to assure to the extent possible that a consistent low concentration of desmopressin (the "target concentration") is delivered to the bloodstream, e.g., generally not more that an amount sufficient to produce a maximum blood concentration of 15+/−3 pg/ml, and preferably less than 10 pg/ml. In many cases the device will deliver an amount of drug which achieves a blood concentration of 5+/−3 pg/ml or less.

The technical difficulty of achieving this goal is presented by the low and variable bioavailability of intranasally administered peptides, including desmopressin, by the very small amounts of active being administered, and by the low target blood concentrations. To promote consistent bioavailability, the concentration of active drug ingredient per spray and the mass (amount or load) of active per spray must be controlled to control precisely the amount of active that enters a nasal passage. This involves formulation of the drug and selection of design parameters of the pump spray using known methods. However, the amount of active that reaches the nasal mucosa can depend, upon other factors, on the physical composition of the spray, i.e., total amount injected, fluid properties such as viscosity, the momentum of the spray, and its droplet size distribution. These properties also are controlled by the chemistry of the formulation and spray nozzle characteristics. Overlaid on these factors determining bioavailability is that only a portion of the fraction of active reaching the mucosa successfully traverses this membrane and enters the blood stream. Unabsorbed drug is swallowed or otherwise degraded and is not bioavailable. Trans-mucosal passage of peptides is enhanced by including in the formulation certain substances that act as permeation enhancers. Of course, inconsistent spray procedure and the patient's particular nasal anatomy also play a part, but the inconsistency in drug uptake due to these factors cannot be controlled except by physician and/or packaging instructions for use that are explicit and clear and followed by the patient.

Applicants discovered that it is possible to safely administer desmopressin by producing an intranasal spray dispenser exploiting these design principles in combination as disclosed herein.

A product designed, for example, to treat nocturia (urinary voiding at night interrupting sleep) in adults, to treat bed wetting in children (primary nocturnal enuresis), or to prevent bed wetting by a person suffering from incontinence, ideally would be taken by the patient after urinating at bedtime. Ideally the dose would suppress urine production for at least five hours, ideally six to six and a half, and possibly as much as eight. A product designed to interrupt urine production for a few hours during the day, such as to take a car trip for three or four hours, should interrupt urine production for two-three hours. At the end of the antidiuretic interval the healthy body seeks homeostasis rapidly and urine is produced normally. Thus, the urge to urinate returns in the next hour or next few hours. The products described herein of course also may be used, preferably under the care of a physician, for more serious disease such as central diabetes insipidus.

Of course, all of the times recited above are approximate, as the duration of antidiuresis achieved in a given person taking a given dose will have a certain inevitable variability. However, the intent and effect of the practice of the invention is to assure to the extent possible that a dose designed to last overnight does not in fact produce only three hours of antidiuresis, resulting in early waking, or involuntary voiding. More important, the effect of practice of the invention is to minimize the possibility that the interval of antidiuresis lasts unexpectedly long, e.g., 10 or 12 hours, resulting in an awake patient drinking liquids, and possibly developing hyponatremia.

The urine production suppression begins when the patient's desmopressin blood concentration exceeds the activation threshold of the water channels in the proximal kidney tubules, and ends when the concentration falls below that threshold. The exact concentration which is sufficient in a given individual to activate the water channels will vary, and it is so low that it is hard to measure with precision, but as disclosed in U.S. Pat. No. 7,405,203, experiments suggest the threshold is somewhat less than 1.0 pg/ml, or about 0.5 pg/ml, and possibly somewhat lower.

Table 1 illustrates certain important features of various embodiments of the invention. Referring to the Table, it discloses dosage parameters, ranges of maximum expected blood concentrations, the average weight of members of various patient populations, and expected durations of antidiuresis for each population. All listed dose forms are exemplary only and should not be regarded as limiting, except as otherwise indicated in the claims. All these products assume that one spray equals one dose. Of course multiple sprays could be employed to achieve the same dose and this may be desirable as promoting consistent uptake.

The first two products exemplify alternative ways to achieve antidiuresis for the treatment of nocturia in adult males. Both generate a $C_{max}$ of about 5-8 pg/ml, but the first has a 10% bioavailability and delivers 1.0 to 1.6 µg desmopressin per spray, while the second has a bioavailability of about 20%, so requires only about half as much active per spray. Both deliver about 100 to 160 ng of drug to the patient's bloodstream, and this amount circulates to produce the desired blood concentration ($C_{max}$) Exemplary product 3 is designed to treat enuresis in children. If the child has an average weight of 35 kg, he or she will experience 5 to 7 hours of antidiuresis with an intranasal dose of 300-400 ng and a 15% bioavailability. This will deliver 45-70 ng desmopressin to the child's circulation and produce the desired 5-8 pg/ml concentration that will fall below the threshold concentration as normal clearance mechanisms reduce drug concentration until the threshold is passed five to seven hours later. Exemplary product 4 is designed to induce short duration urine suppression in, e.g., females averaging 60 kg. In this case, the interval desirably is short, e.g., about three hours. This can be achieved by intranasal administration of a dose that will produce a $C_{max}$ of 1-2 pg/ml. This blood concentration can be achieved reliably with proper use of a dispenser delivering a 100-200 ng load characterized by a 15% bioavailability. Products 5 and 6 illustrate still other products designed for treatment of nocturia or other therapies involving temporary suppression of urine production in a 60 kg woman or a 200 kg man.

the digestive system where the administered desmopressin is essentially lost. Intranasal delivery of droplets in a stream or otherwise along a central axis is best avoided: substantial variation in bioavailability is possible, depending on whether the angle of administration leads the droplets to the conchae or to the pharynx. In contrast, the present invention produces spray plumes where relatively few droplets travel along a central axis. As a result, the dispensed desmopressin is deposited preferentially upon the mucosal membranes of the nasal cavity, minimizing absorption variability. An additional advantage: by minimizing transit of the desmopressin formulation through the pharynx, unpleasant tastes or aftertastes that may be associated with the desmopressin formulation are minimized.

TABLE 1

| | Patient Population | Duration of Antidiuresis | Mass of Drug per Spray | Bioavailability | Drug Delivered to Bloodstream | Cmax |
|---|---|---|---|---|---|---|
| 1 | 70 kg adults | 5-7 hr | 1.0-1.6 μg- | 10% | 100-160 ng | 5-8 pg/ml |
| 2 | 70 kg adults | 5-7 hr | 500-800 ng | 20% | 100-160 ng | 5-8 pg/ml |
| 3 | 35 kg children | 5-7 hr | 300-480 ng | 15% | 45-70 ng | 5-8 pg/ml |
| 4 | 60 kg adult females | 3 hr | 100-200 ng | 15% | 15-35 ng | 1-2 pg/ml |
| 5 | 60 kg adult females | 5-7 hr | 400-700 ng | 20% | 80-140 ng | 5-8 pg/ml |
| 6 | 100 kg adult males | 5-7 hr | 3-4.5 μg | 5% | 140-220 ng | 5-8 pg/ml |

Turning now to the details of the design of the safety dispenser, suitable drug reservoirs such as glass bottles and plastic squeeze bottles are widely available and used for pharmaceutical dispensing. Preferably the reservoir and the spray pump are disposable. Finger actuated pump sprays comprising plastic parts and metal springs are available commercially, for example, from Pfeiffer of America, Inc, Princeton N.J. These are available in designs to control drop size distribution to meet various specifications. For use in intranasal products the pumps typically deliver a 100 μl load in a narrow spray pattern, although in various embodiments of the invention the volume per spray may be varied, e.g., between 50 μl and 150 μl. Many different such metered drug pump designs can be adapted for use in the invention. Non limiting examples are disclosed in U.S. Pat. Nos. 4,860,738, 4,944,429, 6,321,942, 6,446,839, 6,705,493, 6,708,846, 6,772,915, and 7,182,226.

The spray pattern delivered by the pump can substantially affect the reproducibility of the bioavailable dose of drug delivered. As shown in FIG. 1, the nostrils open into a nasal cavity that is larger toward the front of the head and extends toward the back. The nasal cavity includes the "conchae," a series of protrusions dividing the nasal airway from front to back. These conchae are covered with mucosal membranes and together constitute the majority of the mucosal membranes in the nasal cavity. At the far end of the nasal cavity is the top of the pharynx (the "nasopharynx"), which extends down toward the esophagus.

When a nasal spray is administered, droplets deposited upon the mucosal membranes of the nasal cavity, such as those on the conchae, permit transmucosal delivery of desmopressin with a substantial and reliable bioavailability. In contrast, droplets that reach the pharynx are likely to be cleared more quickly by mucosal flows, eventually reaching In addition to the beneficial spray pattern, the spray's divergence angle as it exits the device; the spray's cross-sectional ellipticity and uniformity; and the time evolution of the developing spray can contribute to limiting the variation in $C_{max}$ produced by the dispensing device. An apparatus for measuring plume geometry and spray pattern is available from Proveris Scientific Corporation of Marlborough, Mass.

Figure 2B:
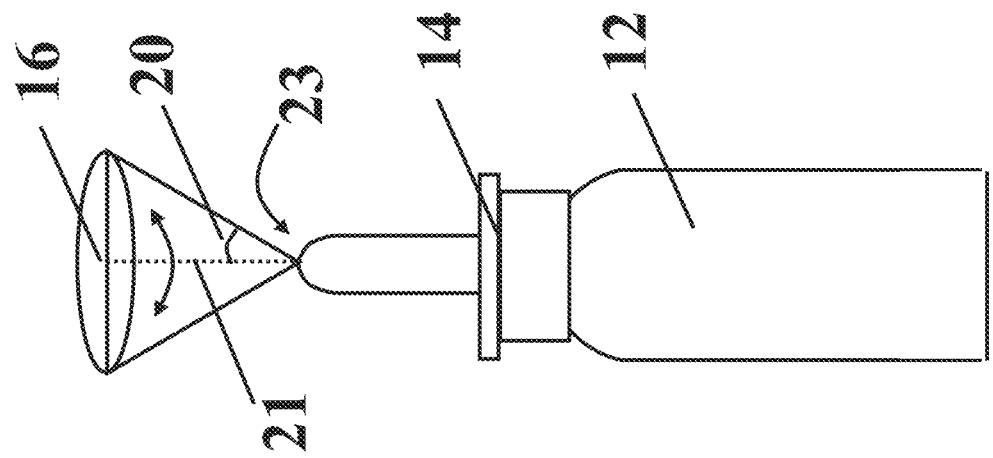
FIGS. 2A-B show schematic diagrams of a nasal spray device for use with the present invention.
Figure 2A:
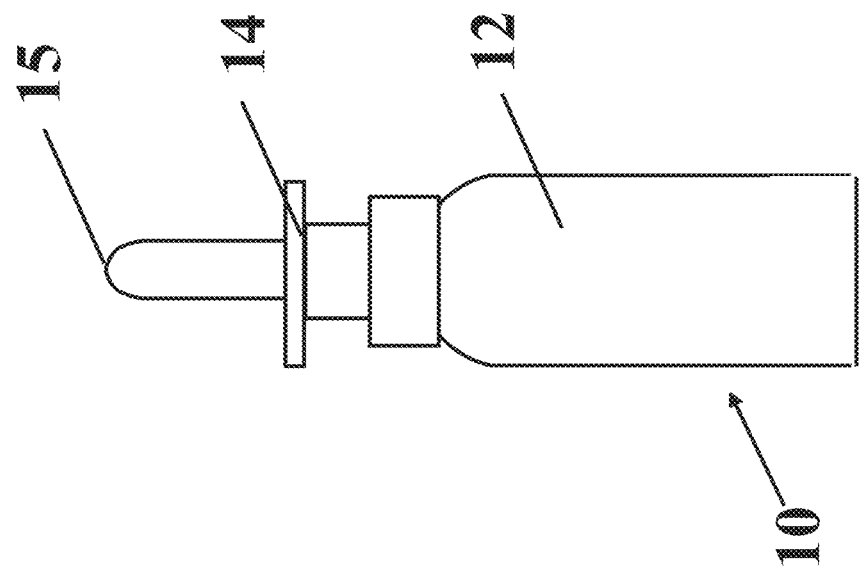

A schematic diagram of a spray device suitable for use with the present invention is shown in FIGS. 2A-B. FIGS. 2A and 2B show a safety dispenser 10 before engagement (FIG. 2A) and after engagement (FIG. 2B). The safety dispenser 10 includes a reservoir 12, in this case a bottle, into which the desmopres sin is placed, and a pump 14 attached to reservoir 12 and in fluid connection with the desmopressin preparation in reservoir 12. When the pump 14 is actuated or engaged, it forces a spray plume 16 of desmopres sin through outlet 15 of the pump 14. The spray plume 16 has angle of ejection 20 as it leaves the pump 14. The spray plume 16 is formed of the moving droplets of the desmopressin preparation, together defining a conical volume having a central axis 21 and an apex 23 adjacent the nozzle of the spray device.

The safety dispenser of the present invention permits a plume with improved characteristics compared to plumes produced by traditional nasal spray devices. As shown in FIGS. 3A-D, the stages in the formation of the spray plume of a traditional nasal spray device are the formation phase, the stable phase and the dissolution phase. During the formation phase (FIG. 3A), large drops of liquid are initially produced and travel upward in a linear fashion. During the stable phase (FIG. 3B), formation of a fine mist occurs. In the dissolution phase, the vacuum pressure in the bottle starts to drop, causing the plume to narrow and collapse (FIG. 3C). Finally, at the end stage of the plume (FIG. 3D), the spray at the formation and dissolution stages lands in the center of the plume, once again producing a linear stream of liquid.

In contrast, FIGS. 4A-D shows formation of the plume of the present invention. As soon as the hydraulic pressure is higher than the spring force, the tip seal (valve) opens and the liquid is dispensed via the nasal spray actuator. The geometry of the nozzle allows the product to be broken up into a fine mist, creating a conical plume even from the formation stage (FIG. 4A), unlike the linear stream that is initially formed using a traditional nasal spray device. The conical plume is maintained throughout the stable phase (FIG. 4B) and the dissolution stage (FIG. 4C), unlike the linear stream that is formed during the dissolution stage using a traditional nasal spray device. At the end of the dispensing stroke, the hydraulic pressure drops and the spring of the differential valve in the nasal actuator closes the tip seal right below the orifice, shutting off the plume (FIG. 4D). Formation of a conical plume throughout the stages of plume formation increases contact of the droplets with intraluminal mucosal surfaces, and therefore can increase bioavailability and reduce variation from one administration to the next.

Figure 5:
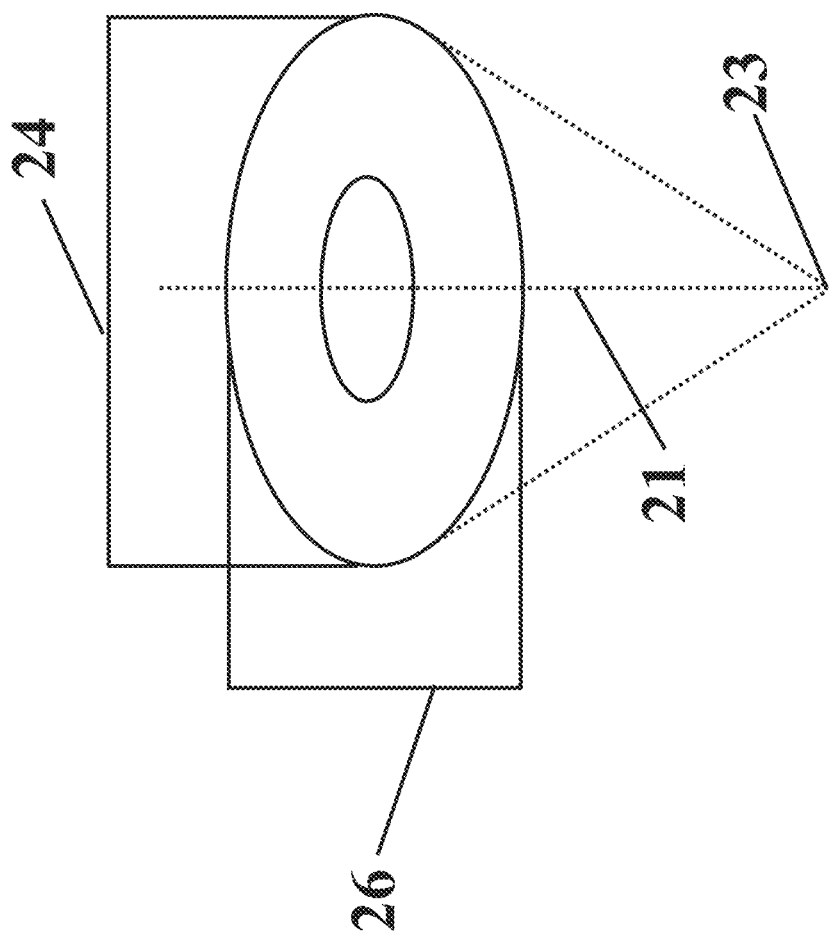
FIG. 5 is a schematic diagram of a spray pattern.

The characteristics of a spray plume can also be evaluated by analyzing the spray pattern. Returning to FIGS. 2A-B, a spray pattern is determined by taking a photograph of a cross-section of the spray plume 16 at a predetermined height of the plume. A schematic depiction of a spray pattern is shown in FIG. 5. The spray pattern of FIG. 5 is elliptical with a major axis 24 and a minor axis 26.

Figure 6:
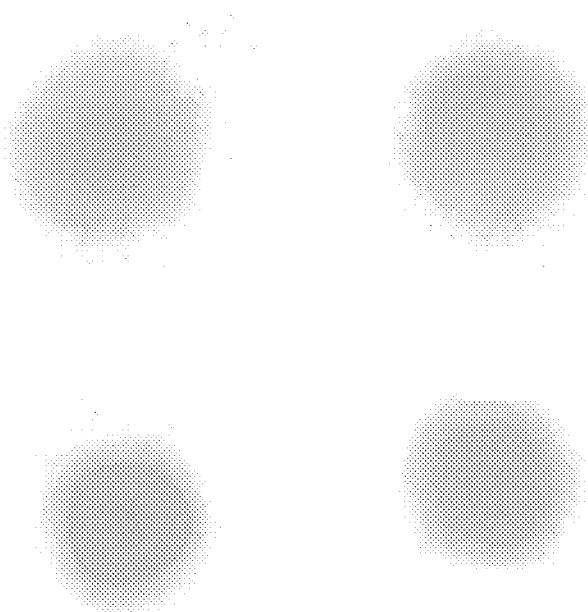
FIG. 6 shows four spray patterns of a saline solution.

Exemplary spray patterns resulting from spraying a standard saline solution are shown in FIG. 6. Four actuations of a saline spray are depicted. The spray pattern of the saline spray shows that the saline solution is distributed evenly throughout the cross-section of the spray plume.

Figure 7:
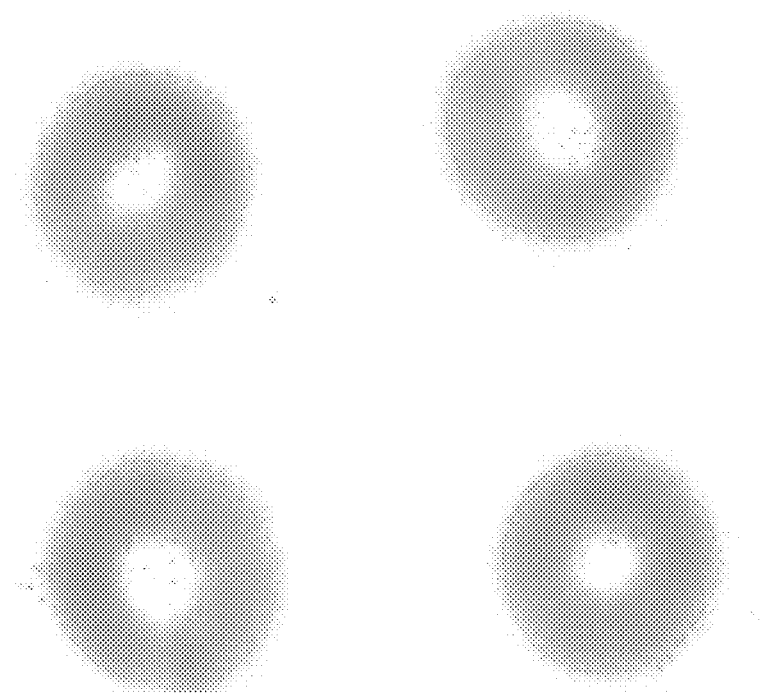
FIG. 7 shows four spray patterns of a desmopressin placebo.

In contrast, spray patterns achieved when dispensing the formulation described in example 2 (but omitting the desmopressin) using identical dispensers are markedly different, as shown in FIG. 7. Four exemplary actuations are depicted. Unlike the spray patterns in FIG. 6, in which droplets were present throughout the cross-section of the plume, the droplets of the desmopressin placebo are reproducibly concentrated on the outside perimeter of the spray plume. The desmopressin placebo is an emulsion that has a lower surface tension than a typical nasal spray. Without wishing to be bound by theory, it is believed that the lowering surface tension provides smaller droplets that are more reliably ejected along the perimeter of the spray plume.

The currently preferred spray apparatus is a pump available from Pfeiffer of America (Princeton, N.J.), marketed as the "Advanced Preservative Free" or "APF" nasal pump, fitted to a 5.0 ml glass bottle. It delivers a metered, 100 μl load in a narrow spray pattern. The pump includes a valve in the tip and a microfilter to prevent microbial contamination. The valve seals the tip until actuation of the pump creates sufficient hydraulic pressure to overcome a spring force, at which point the valve opens and the formulation is dispensed as a mist. As delivery of the dose completes and the hydraulic pressure diminishes, the spring reseals the tip, stopping further release of the drug.

Preferably, to promote consistency, the spray delivers the active formulation as a multiplicity of droplets with an average volume distribution in the range of 30 μm for D10 to about 200 μm for D90. This means that about 10% of the droplets are smaller than about 30 μm in diameter and 90% are smaller than 200 μm in diameter. Other distributions may be used. Very small droplets tend to be inhaled and may or may not reach the circulation. Large droplets may not penetrate the nostril lumen sufficiently and may result in leakage and loss. Such metered pumps assure that, with proper injection protocol, each use results in expelling a metered amount and that a relatively constant amount ends up in contact with the nasal mucosal surface.

The composition disposed within the reservoir comprises desmopressin, also called Anti-Diuretic Hormone, 1-desamino-8-D-arginine vasopressin, or dDAVP. It is a water soluble vasopressin analog having a molecular weight of 1069.23. Drug grade material is widely commercially available as the acetate salt. The term desmopressin, as used herein, refers to 1-desamino-8-D-arginine vasopressin and all other such analogs having antidiuretic activity, including analogs of active allelic variants of human vasopressin, and including other anions. See, for example U.S. Pat. No. 3,980,631, and U.S. Pat. No. 4,148,787.

The composition also necessarily includes at least one substance that acts as a permeation enhancer, that is, a substance which increases the net peptide transport across the mucosal membranes from the nasal lumen to the capillary bed behind it. Many permeation enhancers are known in the art, and there are many ways to formulate such enhancers with peptide drugs so as to effectively increase their bioavailability. Permeation enhancers generally function by opening the tight junctions formed between epithelial cells of the mucosal membrane, thereby allowing diffusion of therapeutic agent into and through the membrane.

Significant research has been conducted to enhance bioavailability across nasal membranes directed toward developing intranasal administration of insulin. See, for example, U.S. Pat. No. 5,112,804 and U.S. Pat. No. 7,112,561. The learning from these efforts can be applied in the formulation of desmopressin compositions to improved trans mucosal bioavailability. Generally, the enhancers used to promote insulin transport are more effective to improve trans mucosal desmopressin bioavailability as the target blood concentration of desmopressin is orders of magnitude smaller than effective insulin doses, and desmopressin is a much smaller polypeptide (MW 1069 vs. 5808).

The permeation enhancer used in the composition of the invention may include any entity that is compatible with peptide administration and facilitates absorption of the peptide across the nasal mucosal membrane. The currently preferred enhancers are the so called Hsieh enhancers. See U.S. Pat. Nos. 5,023,252, 5,731,303, 7,112,561, and 7,244,703. These are macrocyclic esters, diesters, amides, diamides, amidines, diamidines, thioester, dithioester, thioamides, ketones or lactones. The macrocyclic moiety often contains at least twelve carbon atoms. The preferred group are the cyclopentadecanolides disclosed in U.S. Pat. Nos. 5,023,252 and 7,112,561. Cyclopentadecalactone or cyclohexadecanone are currently preferred, see U.S. Pat. No. 7,244,703. The currently preferred species is cyclopentadecanolide, sold under the trade name CPE-215 by CPEX, Inc of Exeter, N.H.

Many other less preferred enhancers disclosed in the art as being useful in enhancing passage through mucosal tissue barriers such as the skin, GI tract, or other mucosal surfaces also may be adapted for use in the products of the invention. Non limiting examples include bile salts and other fatty acids, sugar esters or sugar alcohol esters such as sorbitan esters of long chain aliphatic acids (See U.S. Pat. Nos. 5,122,383; 5,212,199 and 5,227,169). Membrane (skin) permeation enhancement using aliphatic alcohol esters of lactic acid is disclosed in U.S. Pat. No. 5,154,122. U.S. Pat. No.

5,314,694 discloses use of esters of fatty acid alcohols, i.e. lauryl alcohol and lactic acid. Potentially useful permeation enhancers include bile salts such as sodium cholate, sodium glycocholate, sodium glycodeoxycholate, taurodeoxycholate, sodium deoxycholate, sodium taurodihydrofusidate, taurocholate, and ursodeoxycholate, sodium lithocholate, chenocholate, chenodeoxycholate, ursocholate, ursodeoxycholate, hyodeoxycholate, dehydrocholate, glycochenocholate, taurochenocholate, and taurochenodeoxycholate. Also useful are other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, or natural or synthetic derivatives of bile salts. U.S. Pat. No. 5,719,122 discloses polyglycolysed glycerides which may be employed as permeation enhancers and include saturated polyglycolysed glycerides consisting of $C_8$-$C_{18}$ glycerides and polyethylene glycol esters, such as those available under the trade names Gelucire®, e.g. Gelucire® 33/01, 35/10, 37/02 or 44/14; unsaturated polyglycolysed glycerides consisting of $C_{16}$-$C_{20}$ glycerides and polyethylene glycol esters such as those available under the trade name Labrafil®, e.g. Labrafil® WL 2609 BS, or M 2125 CS; and saturated polyglycolysed $C_8$-$C_{10}$ glycerides, such as those available under the trade name Labrasol. A mixture of such polyglycolysed glycerides may be employed, e.g., Gelucire 44/14 and Labrasol.

Permeation enhancers suitable for use in the formulation of drug preparations which enter the bloodstream via the GI tract also potentially may be adapted for use in the present invention. These, without limitation, include those disclosed in U.S. 20030232078 such as ethylene-diamine tetra-acetic acid (EDTA), bile salt permeation enhancers such as those noted above and fatty acid permeation enhancers, such as sodium caprate, sodium laurate, sodium caprylate, capric acid, lauric acid, and caprylic acid, acyl carnitines, such as palmitoyl carnitine, stearoyl carnitine, myristoyl carnitine, and lauroyl carnitine, and salicylates, such as sodium salicylate, 5-methoxy salicylate, and methyl salicylate. U.S. Pat. Nos. 4,548,922 and 4,746,508 also discloses a system for delivering proteins and polypeptides by intranasal or other transmucosal routes using low toxicity permeation enhancers of the amphiphilic steroid family, e.g. fusidic acid derivatives, to promote efficient transport of the drug across the mucosal surface. The disclosed compositions, which are generally water-based, have been demonstrated to be useful for the intranasal delivery in humans of a variety or proteins and peptides, including insulin, human growth hormone, and salmon calcitonin, and are potentially useful in the compositions component of the dispensers of the invention.

It is very difficult to predict which enhancer will work best for a given drug. For permeation enhancement of desmopressin, the actual effectiveness of an enhancer should be verified by routine experiments of a nature well known to the skilled artisan, e.g., using the porcine or rat model. The amount of permeation enhancer included in the formulation component of the present invention will generally range between about 1 wt % to about 30 wt %. The precise nature and amount of enhancer will vary depending on, for example, the particular permeation enhancer or enhancer composition selected, and on the nature of other components in the formulation. Thus, the concentration of the permeation enhancer within the medicament medium may be varied depending on the potency of the enhancer. The upper limit for enhancer concentration is set by toxic effect to or irritation limits of the mucosal membrane. The solubility of the enhancer within the medicament medium may also limit enhancer concentration.

The composition may be formulated as a simple, typically mildly acidic, aqueous solution of desmopressin, containing a water-soluble permeation enhancer molecule or multicomponent permeation enhancer composition. Alternatively, the composition may be formulated as a two phase system with a hydrophobic and a hydrophilic phase. The composition of course may include other conventional components such as emulsifiers or surface active agents to aid in stabilization and enhancement of drop formation within the structure of the spray nozzle, preservatives so as to enhance shelf life or permit room temperature storage, stabilizers, osmolarity controls (salts), and a buffer or a buffer system. Formulations are best optimized empirically. Any given candidate formulation may be tested by intranasal administration to experimental animals, e.g., pigs or rats, or with proper approvals after appropriate pre-clinical testing, to humans. Periodic sampling of blood will reveal the desmopressin concentration at various times post administration so as to permit calculation of $C_{max}$ and other variables and the consistency of delivery to the circulation among successive doses both inter patient and intra patient.

EXAMPLES

Example 1: Example of Formulation Testing Protocol

This example describes how to test a given candidate formulation for efficiency in transport across nasal membranes. It assumes testing of compositions comprising water soluble permeation enhancers "A" and "B" and seeks to measure the fraction of desmopressin that permeates the nasal mucosa and enters the bloodstream in a low dose range, and how this bioavailability is altered as a function of the identity and concentration of these different enhancers.

Thus, by way of example, four formulations may be prepared having the following compositions.

TABLE 2

| Nasal formulation test compositions | | | | |
|---|---|---|---|---|
| Formulation | 1 | 2 | 3 | 4 |
| Desmopressin (µg/ml) | 2 | 2 | 2 | 2 |
| Na$_2$HPO$_4$ (mM) | 16 | 16 | 16 | 16 |
| Citric acid (mM) | 8 | 8 | 8 | 8 |
| NaCl (mM) | 145 | 145 | 145 | 145 |
| pH | 4.9 | 4.9 | 4.9 | 4.9 |
| Permeation enhancer mg/ml | "A" 2 mg/ml | "A" 10 mg/ml | "B" 2 mg/ml | "B" 10 mg/ml |

A 10 µl drop of each formulation will contain 0.02 µg (20 ng) of desmopressin. A drop of a each candidate composition is applied to a nostril in each of three anesthetized rats, weighing, for example, between 225 and 250 grams. Blood is drawn prior to dosing and at 10, 20, 40, 60, and 120 minutes after dosing. The desmopressin concentration of each blood sample is determined using, for example, an immunoassay with sufficient sensitivity at the low pg desmopressin concentrations in the samples. From these data $C_{max}$ can be calculated for each formulation and all compositions tested can be rated for efficient passage of desmopressin across rat nasal mucosal tissue. Promising formulations can be tested further, e.g., by introduction of a spray of a given formulation, volume and desmopressin concentration into the nostril of test pigs. Again, blood samples are drawn and $C_{max}$, AUC, or other measures of drug bioavailability can be determined. These data, in turn, permit preparation of test formulations for use in a phase I clinical trial, with the goal of designing a safety dispenser which when used correctly consistently produces a desmopressin drug concentration within a low dose target concentration range.

Example 2: Exemplary Formulation

Emulsion Stock Solution

To produce an emulsion stock solution, the following ingredients in parts by weight are added to a vessel equipped with a stirring bar, and mixed for 15 minutes at 60-65° C.

180 parts sorbitan monolaurate (Span-20) aqueous solution (12 mg/ml)

30 parts Polysorbate 20 (Tween-20) aqueous solution (2 mg/ml)

400 parts cottonseed oil aqueous emulsion (26.6 mg/ml)

600 parts cyclopentadecanolide (CPE-215) aqueous emulsion (40 mg/ml)

Water to produce 1,500 grams total batch size

After mixing the preparation is homogenized using a high speed mixture at 6500 RPM+ for 20-25 minutes to produce a fine emulsion. This solution is autoclaved to assure sterility.

Buffer Solution

To produce a citric acid buffer stock solution, the following ingredients in parts by weight are added to a vessel equipped with a stirring bar, and mixed for 5 minutes at 60-65° C.

6200 parts water 16 parts anhydrous citric acid aqueous solution (1.85 mg/ml)

76 parts sodium citrate, dihydrate aqueous solution (8.9 mg/ml)

104 parts Polysorbate 20 (Tween-20) aqueous solution (12 mg/ml)

Water to produce 8,500 grams total batch size

Desmopressin Solution

To produce a desmopressin stock solution, 0.111 part desmopressin acetate trihydrate is added to sufficient buffer stock solution to produce 100.0 ml of solution, and stirred until all the desmopressin is dissolved to produce a stock solution having a concentration of 100 μg desmopressin/ml. From this stock solution a 10 μg/ml solution was prepared by dilution.

Aliquots of the 10 μg/ml solution were filtered to eliminate any bacterial contamination and diluted with an equal volume of emulsion stock solution to produce aseptic, preservative free dose forms comprising 5 μg/ml desmopressin, pH 5.5, containing 2% cyclopentadecanolide. These were bottled in sterile pump spray bottles fitted with a Pfeiffer APF pump sprayers that deliver 100 μl per metered spray, or 0.50 μg desmopressin, or 500 ng desmopressin per spray. The liquid contains no detectable microorganisms. The commercially available, disposable Pfeiffer APF pump comprises a mechanism that prevents backfill of potentially contaminated air after the pump has been actuated and thus maintains substantial sterility of each dose dispensed. These were tested on humans to determine the blood concentration they delivered, duration of antidiuresis, their pharmacokinetic properties, etc., as set forth below.

Example 3: Clinical Testing of Prototype Product

A clinical study using a safety dispenser embodying the invention described above in human adult subjects in a water loaded state demonstrated that doses administered intranasally of 500 ng to 2000 ng (one to four sprays) produced antidiuretic effects in a dose proportional relationship for durations of from 2 to 7 hours. Peak blood concentrations ranged from about 1.25 to about 10 pg/ml. None of the test subjects exhibited any drug related decreases in serum sodium.

The open-label preliminary study of the effects and pharmacokinetics of the prototype dispensers was conducted with six male and six female healthy, water loaded, non-smoking volunteer subjects, following the protocol described generally below. In summary, each subject was dosed up to four times over a period of one week with dosing administered every other day. On days one, three, and five subjects were dosed intranasally with escalating doses of the low dose desmopressin nasal spray formulation described above. On day seven, subjects were given a single bolus injection of low dose desmopressin either intradermally or subcutaneously as a comparison. All subjects were screened prior to the first treatment, including evaluations of medical history, complete physical exam including nasopharyngeal exam, serum chemistry including serum osmolality, urinalysis including urine osmolality.

On day one all subjects were asked to have his/her morning void prior to breakfast, and thereafter subjects started the water loading process. Water loading assures that a patient is not generating endogenous vasopressin, and accordingly permits isolation of the effect of exogenous desmopressin. To achieve a steady state diuresis, the subjects were directed to drink a volume of water corresponding to at least 1.5% and up to 3% of body weight. The water loading process started about two hours prior to the dosing of the first subject. Subjects were asked to void every 20 minutes. To ensure continuous water loaded state, the subjects replaced their urinary output loss with an equivalent amount of fluid. Insensible loss was not measured or replaced. When the urinary output rate exceeded 10 ml/min in two consecutive measurements (defined as water loaded state) in the subjects, dosing began. Subjects were maintained in the water loaded state with equivalent fluid intake versus fluid loss.

Each subject then was dosed intranasally with one spray (100 μl containing 0.5 μg of desmopressin) of the nasal spray formulation in the right or left nostril. Urine volume was measured in 20-minute intervals from the start of water loading (at least two hours prior to dosing) to the time the subject's urine output returns to baseline (urinary output level that exceeds 10 mL/minute in three consecutive 20-minute measurements) post dose. Serum osmolality and sodium were measured prior to dosing and at 2, 4, 6 and 8 hours post dose.

Blood sampling for pharmacokinetic determinations was performed at 1, 1.5, 2, 3, 4 and 6 hours post dose. Two seven ml blood samples were collected at each time point. The concentration of desmopressin was determined by a validated radio immunoassay. The concentration of desmopressin in plasma was analyzed for the individual volunteer in each group, by use of non-compartmental methods using the commercially available software WinNonlin™ Pro, ver. 3.2 (Pharsight Corporation, USA). A plasma concentration value below the limit of quantitation ("LOQ") followed by values above the limit was set at 'LOQ/2' for the analysis and for the descriptive statistics on concentrations. Values below LOQ not followed by values above the LOQ were excluded from the analysis, and set to zero in the descriptive statistics on concentrations.

On days two, four, and six the subjects fasted beginning at 8 pm until breakfast the following day and were encouraged to drink one to two liters of water between 7 pm and 9 pm. Thereafter, they were to drink fluid ad libitum until the start of the water loading on the next day.

On day three, the subjects received one spray of desmopressin nasal spray formulation in each nostril (total volume of 200 µl equivalent to 1000 ng of desmopressin). Other than the dose level, all procedures were the same as those described for day one.

On day five, all subjects received a total volume of 2000 ng of desmopressin (one nasal spray in each nostril followed five minutes later by a second spray in each nostril). Other than the dose level, all procedures were the same as those described for day one.

On day seven, three male and three female subjects received a single bolus intra-dermal injection of desmopressin solution (150 µl of 0.8 µg/ml solution equivalent to 120 ng of desmopressin), and the other six subjects received a single bolus subcutaneous injection of desmopressin (150 µl of 0.8 µg/ml solution equivalent to 120 ng of desmopressin). Other than the dosing paradigm, all procedures were the same as described on day one.

Pharmacokinetic parameters were derived from the individual concentration of desmopressin found in blood samples versus time curves of desmopressin, included AUC, and $C_{max}$. Assay values below the limit of detection of the desmopressin immunoassay (<1.25 pg/ml) were set equal to zero for purposes of averaging concentrations. Assay values below the level of detection that occurred between two non-zero concentrations were considered to be "missing" for purposes of calculating the AUC. Blood concentration measurements from the 0.5 µg dose study were not conducted as often unreliable and below the limit of detection. Since the traditional analysis resulted in many subject/treatment combinations not being evaluable for $T_{1/2}$ or AUC, a hypothesis was made that for a given subject, the half-life would be consistent from treatment to treatment. Therefore, as long as one of the three treatments generated an evaluable terminal half-life, that value could be used to extrapolate the AUC for the treatments that did not have evaluable half-lives. Accordingly, an average terminal half-life (Avg $T_{1/2}$) was calculated for each subject that included a treatment with evaluable half-lives in that subject. Ten of the twelve subjects had half-lives evaluable for at least one treatment. The AUC could be calculated for each treatment and subject using the calculated average $T_{1/2}$ value.

It was determined that aside from one anomalous patient, all 11 patients in the study had peak desmopressin drug concentrations at the 2000 ng dose level of between 3.9 and 10 pg/ml. Furthermore, 9 of the 11 achieved drug concentrations between 5.18 and 8.4 pg/ml. This alone illustrates the consistency of the blood concentration achieved using the prototype dispenser described above. Furthermore, as a result of the study, the following AUC and $C_{max}$ values were calculated. The calculated coefficient of variation of each data point is indicated in parentheses.

TABLE 3

|  | 1000 ng Nasally (2 sprays) | 2000 ng Nasally (4 sprays) | 120 ng Subcutaneous Injection | 120 ng Intradermal Injection |
| --- | --- | --- | --- | --- |
| $C_{max}$ pg/ml | N = 7<br>2.79 ± 1.44<br>(51.6%) | N = 12<br>6.24 ± 2.25<br>(36.0%) | N = 6<br>2.77 ± 0.98<br>(35.4%) | N = 6<br>1.93 ± 0.46<br>(23.8%) |
| AUC pg · hr/ml | N = 10<br>5.36 ± 5.92<br>(110.5%) | N = 10<br>11.59 ± 7.9<br>(68.0%) | N = 6<br>7.85 ± 4.21<br>(53.6%) | N = 4<br>4.46 ± 3.09<br>(69.4%) |
| $T_{1/2}$ hr | N = 3<br>1.13 ± 0.30<br>(26.3%) | N = 8<br>1.33 ± 0.56<br>(42.3%) | N = 3<br>2.09 ± 0.32<br>(15.4%) | N = 2<br>1.39 ± 0.61<br>(43.5%) |

Two conclusions may be derived from these data. First, the coefficient of variation of $C_{max}$ of desmopressin administered intranasally using the safety dispenser of the invention for the 1000 ng dose (51.6%) is only about 30% greater than coefficient of variation of $C_{max}$ of a dose of desmopressin administered subcutaneously and designed to produce comparable low blood concentrations. The measured coefficient of variation of $C_{max}$ of desmopressin administered intranasally using the dispensed composition of the invention for the 2000 ng dose (36.0%) is about equal to the coefficient of variation of $C_{max}$ of the subcutaneous dose. These preliminary data support the hypothesis that the formulation of the invention indeed is characterized by a coefficient of variation of $C_{max}$ comparable to that of subcutaneous desmopressin doses designed to achieve a comparable low blood concentration. This is in sharp contrast to commercially available intranasal desmopressin dose forms which, despite being designed to deliver far higher blood concentrations, have a much higher variation in $C_{max}$, a variation that contributes to the stochastic induction of a hyponatremic state.

Second, note that both AUC and $C_{max}$ produced by this formulation dispensed intranasally in accordance with the invention appear to be directly linearly proportional to dose. Thus, the 1000 ng intranasal dose yields a $C_{max}$ of 2.79+/−1.44 pg/ml, while the 2000 ng dose yields a value of 6.24+/−2.25; the 1000 ng intranasal dose results in an AUC of 5.36+/−5.92, which is approximately doubled to 11.59+/−7.9 when the dose is doubled. This suggests that desmopressin can be reliably dispensed intranasally to reproducibly achieve an antidiuretic effect of limited duration without substantial risk of members of a patient population developing hyponatremia. It also suggests that a dispenser delivering a low dose may be used via multiple sprays to achieve any of several antidiuresis durations in a given patient, or that one dispenser may be sold to service different patient populations provided there is proper instruction for how many sprays should be used to produce a given duration of effect in a given population.

The results of this study suggest that the low-dose desmopressin nasal spray embodying the invention provides improved, more reproducible pharmacokinetic parameters at relatively consistent low blood concentrations, and delivers a $C_{max}$ proportional to the doses administered.

The urine output and urine osmolarity was measured just prior to nasal administration of 2000 ng of the pharmaceutical composition of desmopressin and for a period of up to about 10 hours (600 minutes) after administration. FIG. 8 shows the mean urine output for male and female subjects. As evidenced by the data, the urine output fell to less than 8 ml/minute within 20 minutes after administration of the desmopressin by nose (in water loaded individuals). Urine output remained less than 8 ml/minute for a period ranging up to about 400 minutes after administration. FIG. 9 shows the mean urine osmolarity for the same group of male and female subjects as in FIG. 8. Urine osmolarity increased to greater than about 400 mOsmol/kg within 40 minutes after administration of 2 μg of desmopres sin nasally and remained greater than about 400 mOsmol/Kg for about 250 minutes after administration of the desmopressin by nose.

A second separate study in adult patients with nocturia established that doses of 500 and 1000 ng (one or two sprays administered intranasally) produced dramatic therapeutic decreases in the number of night time urinary voids equal to or less than one per night in 41 of 43 patients. Serum sodium levels remained within normal limits throughout treatment.

Example 4: Spray Pattern Testing

To evaluate the characteristics of spray plumes of the desmopressin formulation, SprayVIEW instrumentation operating through Proveris's Viota® software platform was used. A spray pattern was determined by taking a photograph of a cross-section of the spray plume above a predetermined height of the plume. Spray pattern measurements included major axis, minor axis, ellipticity, inclusion, inclination, Dmin, Dmax, ovality, perimeter, area, and % area. The plumes were generated using a pump available from Pfeiffer of America (Princeton, N.J.) and marketed as the "Advanced Preservative Free" or "APF" nasal pump.

Figure 10C:
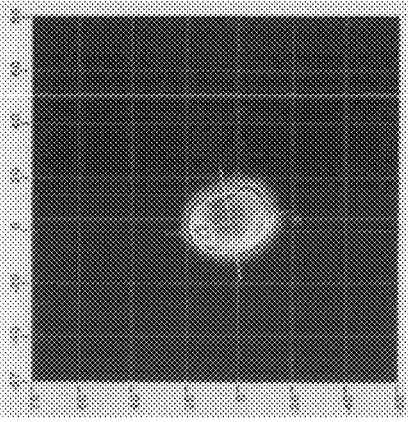
FIGS. 10A-F show spray patterns created in each of six actuations of a spray device containing desmopressin.
Figure 10F:
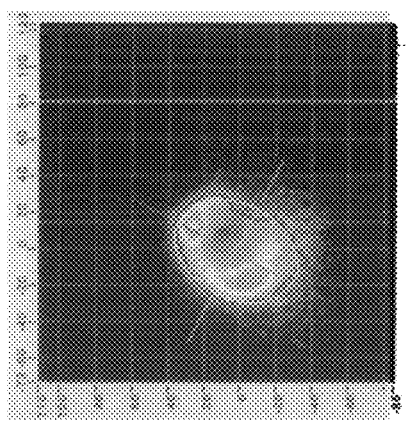
Figure 10B:
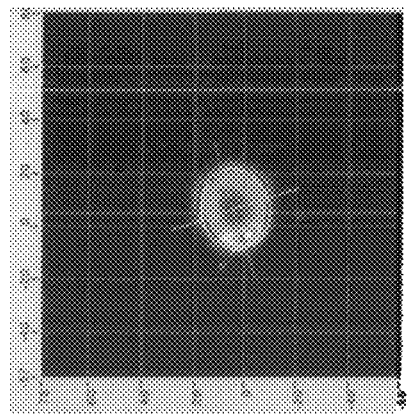
Figure 10E:
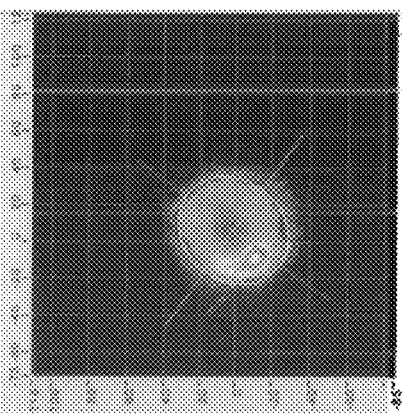
Figure 10A:
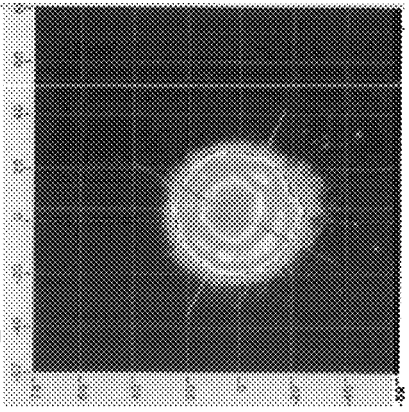
Figure 10D:
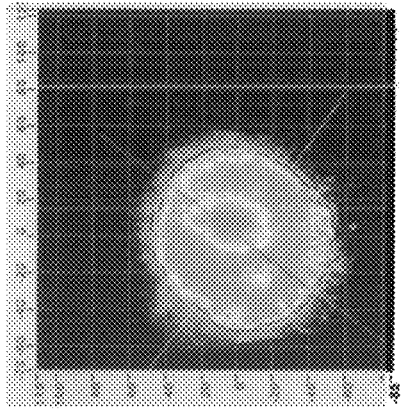

FIGS. 10A-F show exemplary spray patterns created in each of six actuations of a nasal spray device containing desmopres sin. FIGS. 10A-10C show a spray pattern measured from 3 cm above the tip of the device, and FIGS. 10D-10F show a spray pattern measured from 6 cm above the tip of the device. Areas of the cross section with high and intermediate droplet densities are shown in lighter shades of grey and white. Areas of the cross section with the lowest droplet densities are shown in darker shades of grey and black. Each spray pattern shows that the density of droplets is higher along the outer perimeter of the plume, and lower in the center of the plume. Table 4 shows the spray pattern measurements of FIGS. 10A-F.

distribution. "% RSD," refers to the percent relative standard deviation, the standard deviation divided by the mean of the series and multiplied by 100, also known as % $C_V$.

TABLE 5

Droplet Size Distribution by Laser Diffraction

| Shot | Bottle | Diameter | | | Span | Volume < 10 μm (%) |
| --- | --- | --- | --- | --- | --- | --- |
| | | D10 | D50 | D90 | | |
| 3 cm Shot 6 | 1 | 46.7 | 134.5 | 308.8 | 1.9 | 0.2 |
| | 2 | 27.4 | 69.2 | 168.4 | 2.0 | 0.5 |
| | 3 | 27.2 | 66.0 | 162.2 | 2.0 | 0.5 |
| | Average | 33.8 | 89.9 | 213.1 | 2.0 | 0.4 |
| | RSD (%) | 33.2 | 43.0 | 38.9 | 2.7 | 51.1 |
| 3 cm Shot 29 | 1 | 25.8 | 59.1 | 143.8 | 2.0 | 0.7 |
| | 2 | 23.5 | 55.0 | 141.0 | 2.1 | 0.8 |
| | 3 | 26.4 | 62.8 | 158.6 | 2.1 | 0.6 |
| | Average | 25.2 | 59.0 | 147.8 | 2.1 | 0.7 |
| | RSD (%) | 6.0 | 6.7 | 6.4 | 3.6 | 18.2 |
| Average | | 29.5 | 74.4 | 180.5 | 2.0 | 0.5 |
| RSD (%) | | 29.0 | 40.1 | 35.3 | 3.4 | 40.9 |
| 6 cm Shot 6 | 1 | 37.0 | 84.1 | 242.2 | 2.4 | 0.2 |
| | 2 | 25.9 | 48.7 | 112.9 | 1.8 | 0.5 |
| | 3 | 31.5 | 55.3 | 135.1 | 1.9 | 0.4 |
| | Average | 31.5 | 62.7 | 163.4 | 2.0 | 0.4 |
| | RSD (%) | 17.7 | 30.0 | 42.3 | 17.5 | 40.3 |
| 6 cm Shot 29 | 1 | 40.1 | 110.3 | 285.7 | 2.2 | 0.2 |
| | 2 | 26.9 | 47.3 | 96.0 | 1.5 | 0.6 |
| | 3 | 28.5 | 51.7 | 111.5 | 1.6 | 0.5 |
| | Average | 31.8 | 69.8 | 164.4 | 1.8 | 0.4 |
| | RSD (%) | 22.6 | 50.4 | 64.1 | 23.0 | 52.9 |
| Average | | 31.7 | 66.2 | 163.9 | 1.9 | 0.4 |
| RSD (%) | | 18.2 | 38.5 | 48.6 | 19.6 | 43.5 |

The disclosures of all of the patent publications referred to herein are incorporated herein by reference.

Other embodiments are within the following claims:

The invention claimed is:

1. A method of inducing an antidiuretic effect in a patient, the method comprising intranasally administering to the

TABLE 4

| | Major axis (mm) | Minor axis (mm) | Ellipticity | Inclusion | Inclination (deg.) | Dmin (mm) | Dmax (mm) | Ovality | Perimeter (mm) | Area | Area % (mm²) |
| --- | --- | --- | --- | --- | --- | --- | --- | --- | --- | --- | --- |
| 9A | 48.7 | 46.4 | 1.051 | 0.046 | 64.8 | 45.3 | 50.6 | 1.118 | 154.8 | 1811.7 | 9.5 |
| 9B | 31.0 | 27.3 | 1.134 | 0.090 | 18.2 | 25.2 | 32.2 | 1.276 | 95.5 | 685.2 | 3.6 |
| 9C | 32.5 | 22.8 | 1.426 | 0.130 | 101.2 | 20.6 | 33.0 | 1.602 | 94.4 | 597.7 | 3.1 |
| 9D | 103.2 | 94.2 | 1.096 | 0.040 | 54.2 | 91.2 | 107.7 | 1.180 | 329.5 | 7723.3 | 20.1 |
| 9E | 63.4 | 55.0 | 1.153 | 0.083 | 54.3 | 52.2 | 68.6 | 1.314 | 205.6 | 2771.9 | 7.2 |
| 9F | 72.3 | 51.0 | 1.417 | 0.130 | 62.8 | 46.4 | 72.4 | 1.562 | 218.1 | 2927.0 | 7.6 |

Table 5 shows droplet size distribution for exemplary desmopressin plumes of the present invention. To determine droplet size distribution, the droplet sizes that resulted from actuations ("shots") of three nasal spray devices ("bottle") were measured by laser diffraction. Measurements were taken from a height of either 3 cm or 6 cm above the tip of the spray device, as indicated.

"$D_{10}$," refers to the diameter of droplet for which 10% of the total liquid volume of sample consists of droplets of a smaller diameter (μm). "$D_{50}$," refers to the diameter of droplet for which 50% of the total liquid volume of sample consists of droplets of a smaller diameter (μm), also known as the mass median diameter. "$D_{90}$," refers to the diameter of droplet for which 90% of the total liquid volume of sample consists of droplets of a smaller diameter (μm).

"Span," refers to measurement of the width of the distribution, in which a smaller value correlates with a narrower patient a composition of matter comprising an intranasal desmopressin dose in the form of a plume ejected over a time interval from the nozzle of a metered dose spray device, the plume comprising a volume of moving droplets together defining a conical volume having a central axis and an apex at the nozzle of the spray device, wherein the droplet density (number of droplets per unit volume) within the conical volume increases in a direction normal to the axis, the droplets together comprising between about 0.05 μg and 5.0 μg desmopressin, the plume serving to increase contact of the droplets with intranasal luminal mucosal surfaces.

2. The method of claim 1, wherein the administering produces a desmopressin concentration no greater than 15+/−3 pg/ml in the bloodstream of the patient.

3. The method of claim 1, wherein the administering produces a desmopressin concentration no greater than 10+/−3 pg/ml in the bloodstream of the patient.

4. The method of claim 1, wherein the administering produces a desmopressin concentration no greater than 7+/−3 pg/ml in the bloodstream of the patient.

5. The method of claim 1, wherein the administering induces antidiuresis for less than about six hours.

6. The method of claim 5, wherein the administering induces antidiuresis for between about 2 and 4 hours.

7. The method of claim 1, wherein the plume is effective to deliver transmucosally sufficient desmopressin to the bloodstream of a patient weighing 70 kg or 35 kg to produce a desmopressin blood concentration less than 18 pg/ml.

8. The method of claim 1, wherein the plume is effective to produce a desmopressin blood concentration less than 15 pg/ml.

9. The method of claim 1, wherein the plume is effective to produce a desmopressin blood concentration less than 10 pg/ml.

10. The method of claim 1, wherein the droplets together comprise between about 0.2 μg and 5.0 μg desmopressin.

11. The method of claim 1, wherein the droplets together comprise about 1.5 μg desmopressin.

12. The method of claim 1, wherein the droplets together comprise about 0.75 μg desmopressin.

13. The method of claim 1, wherein the droplets together comprise about 2 μg desmopressin.

14. The method of claim 1, wherein the droplets further comprise a permeation enhancer.

15. The method of claim 14, wherein the permeation enhancer comprises cyclopentadecanolide.

16. The method of claim 1, wherein the droplets together comprise 1.5 μg desmopressin.

17. The method of claim 1, wherein the droplets together comprise 0.75 μg desmopressin.

18. The method of claim 15, wherein the droplets together comprise 1.5 μg desmopressin.

19. The method of claim 15, wherein the droplets together comprise 0.75 μg desmopressin.

* * * * *